US012751958B2

(12) United States Patent
Ollervides Rubio et al.

(10) Patent No.: US 12,751,958 B2
(45) Date of Patent: Oct. 6, 2026

(54) COMBINATION DRUG FOR THE CONTROL AND MANAGEMENT OF TYPE 2 DIABETES MELLITUS

(71) Applicant: LABORATORIOS SILANES S.A. DE C.V., México City (MX)

(72) Inventors: Paola Yazmín Ollervides Rubio, México City (MX); Sixto Serafin Espinoza León, México City (MX); Ernesto Cuahutencos Escobar, México City (MX); Jorge Alejandro González Canudas, México City (MX)

(73) Assignee: Laboratorios Silanes S.A. de C.V., Mexico City (MX)

( * ) Notice: Subject to any disclaimer, the term of this patent is extended or adjusted under 35 U.S.C. 154(b) by 620 days.

(21) Appl. No.: 18/023,495

(22) PCT Filed: Sep. 2, 2020

(86) PCT No.: PCT/MX2020/050030

§ 371 (c)(1),
(2) Date: Feb. 27, 2023

(87) PCT Pub. No.: WO2022/050832

PCT Pub. Date: Mar. 10, 2022

(65) Prior Publication Data

US 2023/0310462 A1 Oct. 5, 2023

(51) Int. Cl.

| | |
|---|---|
| ***A61K 31/64*** | (2006.01) |
| ***A61K 9/20*** | (2006.01) |
| ***A61K 31/155*** | (2006.01) |
| ***A61K 31/40*** | (2006.01) |

(52) U.S. Cl.

CPC ............ *A61K 31/64* (2013.01); *A61K 9/2013* (2013.01); *A61K 9/2027* (2013.01); *A61K 9/2031* (2013.01); *A61K 9/2054* (2013.01); *A61K 31/155* (2013.01); *A61K 31/40* (2013.01)

(58) Field of Classification Search

CPC ...... A61K 31/64; A61K 31/155; A61K 31/14; A61P 3/10

See application file for complete search history.

(56) References Cited

U.S. PATENT DOCUMENTS

| | | | |
|---|---|---|---|
| 8,143,217 | B2 | 3/2012 | Balkan et al. |
| 2012/0021049 | A1 | 1/2012 | Duarte-Vazquez et al. |
| 2016/0151382 | A1 | 6/2016 | Pickering |

FOREIGN PATENT DOCUMENTS

| | | | | |
|---|---|---|---|---|
| CN | 110218171 | A | 9/2019 | |
| CN | 110256300 | A | 9/2019 | |
| EP | 1208143 | B1 * | 8/2004 | ........... C08K 5/0008 |
| EP | 1715893 | B1 | 7/2009 | |
| EP | 1948149 | B1 | 11/2011 | |
| KR | 20180002460 | A | 6/2016 | |
| MX | 339374 | B | 5/2016 | |
| WO | 2006073197 | A1 | 7/2006 | |
| WO | WO-2010092163 | A2 * | 8/2010 | ................ A61P 9/06 |

OTHER PUBLICATIONS

SED Pharma, Exploring Different Types of Tablets in Pharmacy (2026).*

Rowe et al., Handbook of Phamceutical Excipients,6th Edition, pp. 1-917 (2009).*

K. Hermansen et al., Efficacy and safety of the dipeptidyl peptidase 4 inhibitor, sitagliptin, in patients with type 2 diabetes mellitus inadequately controlled on glimepiride alone or on glimepiride and metformin, Diabetes, Obesity and Metabolism, 2007, pp. 733-745, vol. 9, Blackwell Publishing Ltd.

L. Vilar et al., Effectiveness of adding vildagliptin to the treatment of diabetic patients nonresponsive to the combination of metformin and a sulphonylurea, Arq Bras Endocrinol Metab., 2011, pp. 260-265, vol. 55, No. 4.

C.H. Ho Ahn et al., Efficacy and safety of gemigliptin, a dipeptidyl peptidase-4 inhibitor, in patients with type 2 diabetes mellitus inadequately controlled with combination treatment of metformin and sulphonylurea: a 24-week, multicentre, randomized, double-blind, placebo-controlled study (TROICA study), Diabetes Obes Metab., 2017, pp. 635-643, vol. 19, John Wiley & Sons Ltd.

V. Lukashevich et al., Efficacy and safety of vildagliptin in patients with type 2 diabetes mellitus inadequately controlled with dual combination of metformin and sulphonylurea, Diabetes, Obesity and Metabolism, 2014, pp. 403-409, vol. 16, John Wiley & Sons Ltd.

* cited by examiner

*Primary Examiner* — Kevin E Weddington

(74) *Attorney, Agent, or Firm* — Hudak, Shunk & Farine Co LPA

(57) ABSTRACT

An innovative stable immediate release drug for the treatment, control, and better management of type 2 diabetes mellitus containing a sulfonylurea such as glimepiride, a dipeptidyl peptidase-4 (DPP4) inhibitor such as vildagliptin, and a biguanidine such as metformin. At the same time, this invention allows solving a set of important technological challenges in the manufacture of said drug product due to the physicochemical properties and the difference in dosage of the synergistic combination of the drugs.

15 Claims, 10 Drawing Sheets

COMBINATION DRUG FOR THE CONTROL AND MANAGEMENT OF TYPE 2 DIABETES MELLITUS

FIELD OF THE INVENTION

The present invention belongs to the field of health; particularly, it refers to the pharmaceutical field in the manufacture of drugs for the control and management of type 2 diabetes Mellitus.

BACKGROUND OF THE INVENTION

Diabetes mellitus, commonly called diabetes, is a chronic disease associated with abnormally high levels of glucose in the blood. Diabetes is caused by the pancreas not producing enough insulin and/or the body's cells not responding adequately to insulin. Diabetes is a condition that, according to the World Health Organization, affects about 347 million people, and by 2030, this number is likely to increase more than double. The global increase in diabetes will be due to aging, population growth, increasing obesity trends, unhealthy diets, and sedentary lifestyles (Danaei G, Finucane M M, Lu Y, Singh G M, Cowan M J, Paciorek C J et al. National, regional, and global trends in fasting plasma glucose and diabetes prevalence since 1980: systematic analysis of health examination surveys and epidemiological studies with 370 country-years and 2.7 million participants, *Lancet.* 2011, 378(9785): 31-40.) http://www.who.int/mediacentre/factsheets/fs312/es/).

Type 1 diabetes is characterized by the pancreas ceasing to produce insulin and type 2 diabetes is characterized by the body's inability to use insulin effectively, which is often a consequence of overweight or physical inactivity. Both types of diabetes result in elevated blood glucose levels (hyperglycemia). Treatments for diabetes include monotherapies and combination therapies.

Medical practice indicates that the best treatment to control type 2 diabetes is through calorie restriction and increased physical activity; however, these are difficult to follow and often require the administration of drugs for control. Current therapies for diabetes focus on achieving and maintaining glycaemia as close to normal as possible to avoid microvascular (eye damage, kidney damage, nerve damage, and diabetic foot) and macrovascular (cardiovascular disease, such as heart attacks, strokes, and poor circulation in the lower limbs) complications of the disease.

There are several drugs available for the treatment of type 2 diabetes; so far, biguanides, sulfonylureas, glucosidase inhibitors, and insulin sensitizing agents have been used. These drugs are indicated as monotherapies; however, adverse reactions or side effects such as lactic acidosis have been reported with biguanides, hypoglycemia with sulfonylureas, and diarrhea and severe liver function disorders with glucosidase inhibitors (WO2006073197).

For example, glimepiride is a drug indicated for the treatment of type 2 diabetes in adults as a complement to diet and exercise to improve glycemic control as monotherapy. It may also be indicated for use in combination with metformin or insulin to lower blood glucose in patients with type 2 diabetes whose high blood sugar levels cannot be controlled with diet and exercise.

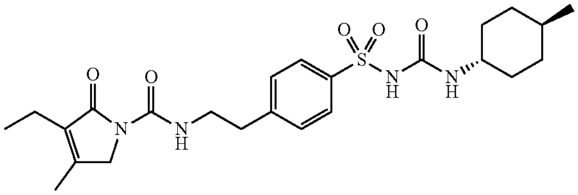 [SMILES: CCC1=C(C)CN(C(=O)NCCc2ccc(S(=O)(=O)NC(=O)N[C@H]3CC[C@H](C)CC3)cc2)C1=O]

According to its biopharmaceutical classification, glimepiride is a type II drug with low solubility and high permeability.

Vildagliptin belongs to a class of orally active antidiabetic drugs known as DPP-IV proteolytic enzyme inhibitors, which have multiple functional benefits beyond simple blood glucose control. One of these is a possible protective effect on pancreatic beta cells, which deteriorate in diabetes. Vildagliptin appears to be safe, very well tolerated, and effective. After a meal, incretin hormones are released from the intestine. The most important incretin hormones are GLP-1 and glucose-dependent insulinotropic polypeptide (GIP). These hormones, secreted in the human small intestine, are responsible for the release of insulin due to increased glucose levels. Unlike agents that promote insulin secretion through glucose-independent mechanisms, GLP-1 dependence on glucose concentration is considered beneficial due to a lower risk of hypoglycemia. GLP-1 also inhibits glucagon secretion and increases beta-cell mass by stimulating proliferation and neogenesis. However, the clinical utility of GLP-1 is limited by its short half-life (2 minutes). GLP-1 is rapidly degraded by the proteolytic enzyme DPP-IV. To enhance GLP-1 activity, inhibition of the DPP-IV enzyme is emerging as a new therapeutic approach in the treatment of diabetes. Administration of vildagliptin increases the ability of GLP-1 to produce insulin in response to elevated blood glucose concentrations, inhibits the release of glucagon after meals, slows the rate of nutrient absorption into the bloodstream, decreases the rate of gastric emptying, and reduces food intake.

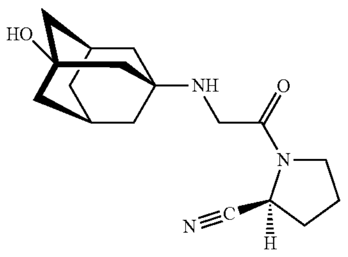

According to its biopharmaceutical classification, vildagliptin is a type III drug with high solubility and low permeability.

Metformin is a biguanide used as an antidiabetic. Its chemical name is 1-(diaminomethylidene)-3,3-dimethyl guanidine. It is frequently employed in the treatment of type 2 diabetes, especially when there is insulin resistance. It is generally recommended at a maximum dose of 3000 mg/day for an adult, and there are 500 mg and 850 mg tablets available (US2012021049A). (US2012021049A). Metformin reduces glucose production in the liver, increases insulin sensitivity in hepatic and peripheral tissue mainly in muscle tissues. It has also been shown to induce weight loss in subjects with type 2 diabetes. (Stumvoll M, Nurjihan N and Perriello G, et al. Metabolics Efects of Metformin in Non-insulin-dependent diabetes mellitus. *N. Engl J Med* 1995; 333:550-554) y (Gerich J E: The genetic basis of type 2 diabetes mellitus: Impaired insulin secretion versus impaired insulin sensitivity. *Endocr Rev* 19:491-503, 1998). The marketed metformin drugs contain metformin hydrochloride. Side effects of metformin hydrochloride include gastrointestinal intolerance (e.g., diarrhea, nausea/vomiting). Metformin hydrochloride is contraindicated in patients with renal disease or renal dysfunction, or acute or chronic metabolic acidosis.

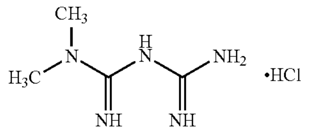

According to its biopharmaceutical classification, metformin is a type III drug with high solubility and low permeability.

In the treatment of type 2 diabetes, the prolonged use of a single drug, the high doses administered for some cases, and the side effects make good control difficult, which is why it is necessary to find new antidiabetic drugs that offer improved glycemic control or combinations of drugs that act by different or complementary mechanisms of action to obtain good glycemic control and management, and fewer side effects.

On the other hand, there is little evidence on the feasibility of combining multiple drugs such as a sulfonylurea, a dipeptidyl peptidase-4 (DPP4) inhibitor, and a biguanidine in a single dose form that is stable and allows the management of chronic diseases such as type 2 diabetes mellitus.

Patent MX 339374 relates to a co-crystal of metformin glimepiridate characterized by physicochemical properties, including a powder X-ray diffraction pattern. Chinese patent application CN201910577018 from WEIHAI DISU PHARMACEUTICAL CO LTD seeks to claim a method for preparing crystalline form I of glimepiride. Novartis AG's MX 301408 patent protects the use of vildagliptin or a salt thereof in combination with insulin in the preparation of a drug to reduce severe hypoglycemic events in a patient suffering from diabetes mellitus. Successively, patent application CN201910562736 describes a metformin hydrochloride crystalline compound characterized by a powder X-ray diffraction pattern.

Novartis AG's MX 275178 patent protects a pharmaceutically compressed or direct compression compressed tablet comprising vildagliptin in free form or in acid salt form wherein at least 60% of the particle size distribution in the tablet is less than 250 microns.

Mexican patent MX 294842 of NOVARTIS AG describes a composition comprising as active ingredients between 1.5 and 20% vildagliptin or a pharmaceutically acceptable salt thereof, between 80 and 98.5% metformin or a pharmaceutically acceptable salt thereof, and further comprising an additional active ingredient, which is a sulfonylurea or a glitazone such as pioglitazone or rosiglitazone. A process for preparing said pharmaceutical composition in layers of a tablet such as bilayers or tri-layers, is also protected.

However, none of them disclose nor suggest a dosage unit or drug product in stable solid pharmaceutical form wherein drugs such as glimepiride, vildagliptin, and metformin, useful for the treatment and control of type 2 diabetes mellitus, are combined. Much less, methods of manufacturing fixed combination drugs of these drugs in a single stable dosage form over time are described nor suggested.

In the search for new treatments, and at the same time, to solve a set of important technological challenges due to the physicochemical properties and the difference in dosage of the synergistic combination of drugs to ensure obtaining a stable drug in the control and management of diabetes, this invention presents the combination of different drugs for the manufacture of an innovative fixed-combination, stable, immediate release drug for the treatment, better control, and management of type 2 diabetes mellitus comprising a sulfonylurea, a dipeptidyl peptidase-4 (DPP4) inhibitor, and a biguanidine (triple therapy).

SUMMARY OF THE INVENTION

This invention relates to a combination drug comprising (a) a sulfonylurea, (b) a dipeptidyl peptidase-4 (DPP4) inhibitor, and (c) a biguanide, or a pharmaceutical salt of any of the same, in pharmaceutically acceptable amounts in the range between 1-4 mg, 50 mg, and 500-1000 mg respectively, in combination with pharmaceutically acceptable excipients and/or vehicles.

The drug of the invention is in solid form and is adapted to be of immediate release.

In one embodiment, the sulfonylurea is in a pharmaceutically acceptable amount, preferably 1 mg, more preferably 2 mg, and more preferably 4 mg.

In another embodiment, the biguanide is in a pharmaceutically acceptable amount, preferably 500 mg, more preferably 1000 mg.

In another embodiment, the combination drug of this invention is preferably in pharmaceutically acceptable amounts of 1/50/500 mg respectively, in combination with pharmaceutically acceptable excipients and/or vehicles.

In another embodiment, the combination drug of this invention is preferably in pharmaceutically acceptable amounts of 2/50/1000 mg respectively, in combination with pharmaceutically acceptable excipients and/or vehicles.

In another embodiment, the combination drug of this invention is preferably in pharmaceutically acceptable amounts of 4/50/1000 mg respectively, in combination with pharmaceutically acceptable excipients and/or vehicles.

The pharmaceutically acceptable excipients and/or vehicles employed for the manufacture of the drug product of this invention are, for example, binders, diluents, disintegrants, lubricants, solvents and/or solubilizers, adsorbents, and coatings.

An additional object of this invention also relates to the use of (a) a sulfonylurea, (b) a dipeptidyl peptidase-4 (DPP4) inhibitor, and (c) a biguanide, or a pharmaceutical salt of any of the same, in pharmaceutically acceptable amounts in the range between 1-4 mg, 50 mg, and 500-1000 mg respectively, in combination with pharmaceutically acceptable excipients and/or vehicles for the manufacture of a drug product useful for the treatment, control, and management of type 2 diabetes mellitus in individuals requiring triple oral therapy, and wherein the sulfonylurea, the dipeptidyl peptidase-4 (DPP4) inhibitor, and the biguanide is preferably glimepiride, vildagliptin, and metformin, or a pharmaceutically acceptable salt of any thereof. Preferably, metformin in its hydrochloride salt form.

The manufacturing process lies in the selection of unit operations, order, and execution time to control the different physicochemical properties of the drugs, whereby the critical operations of the manufacturing process are described in the following detailed description.

In one embodiment, the drug is in a single solid dosage form which is selected from the group comprising a tablet, caplet, granules, lozenges, and pills, preferably in a tablet form.

An innovative, stable, immediate release drug product for the treatment, control, and better management of diabetes Mellitus type 2 containing a sulfonylurea such as glimepiride, a dipeptidyl peptidase-4 (DPP4) inhibitor such as vildagliptin, and a biguanidine such as metformin in its hydrochloride form, is another object of this invention.

In one embodiment of the invention, the pharmacokinetic parameters of $C_{max}$ and area under the plasma concentration curve with respect to time ($ABC_{0-t}$) are determined, which allow characterizing the bioavailability of the drug of this invention from its dosage form, in terms of speed and degree of respective absorption.

DETAILED DESCRIPTION OF THE INVENTION

Definitions

Figure 1:
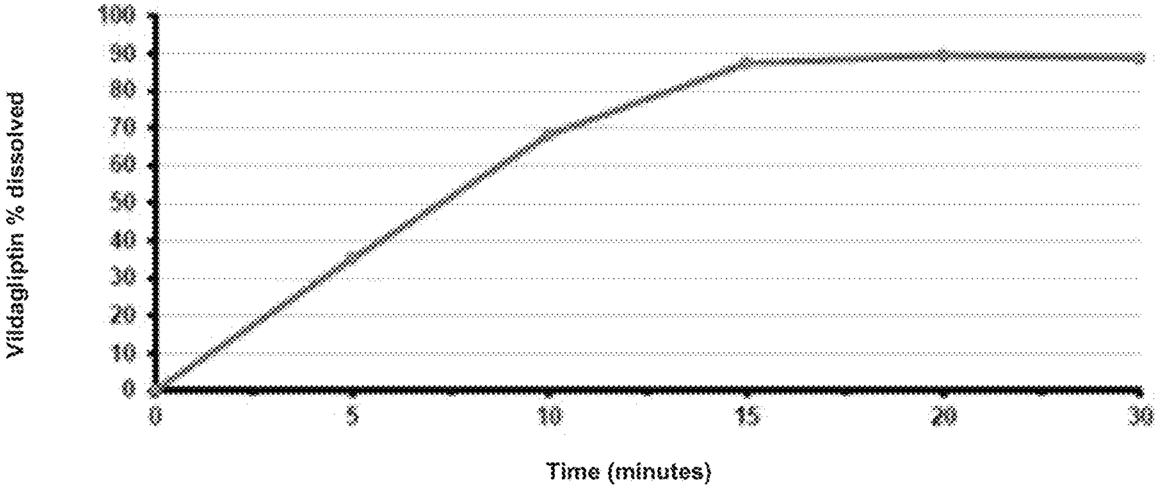
FIG. 1. Vildagliptin dissolution profile of the combination drug comprising glimepiride 4 mg/vildagliptin 50 mg/metformin hydrochloride 1000 mg, FIG. 2. Vildagliptin dissolution profile of the combination drug comprising glimepiride 2 mg/vildagliptin 50 mg/metformin hydrochloride 1000 mg.
Figure 2:
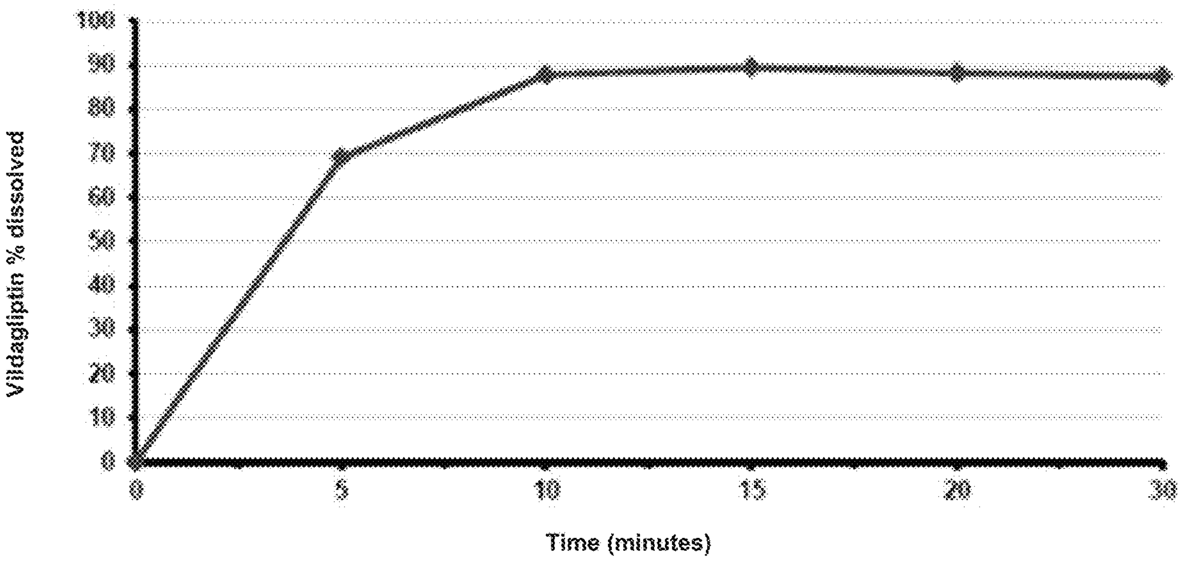
Figure 3:
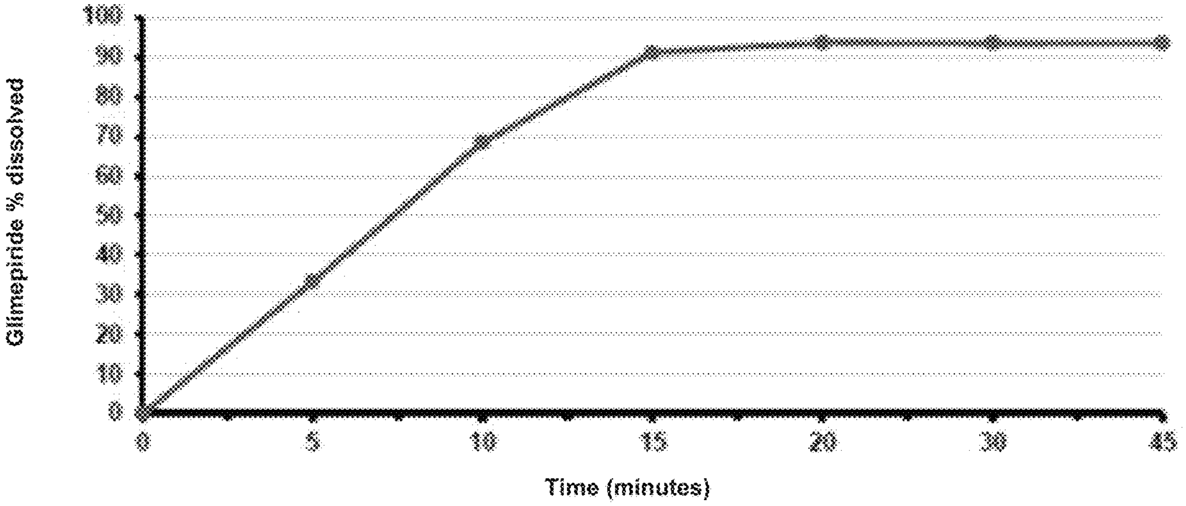
FIG. 3. Glimepiride dissolution profile of the combination drug comprising glimepiride 4 mg/vildagliptin 50 mg/metformin hydrochloride 1000 mg.
Figure 4:
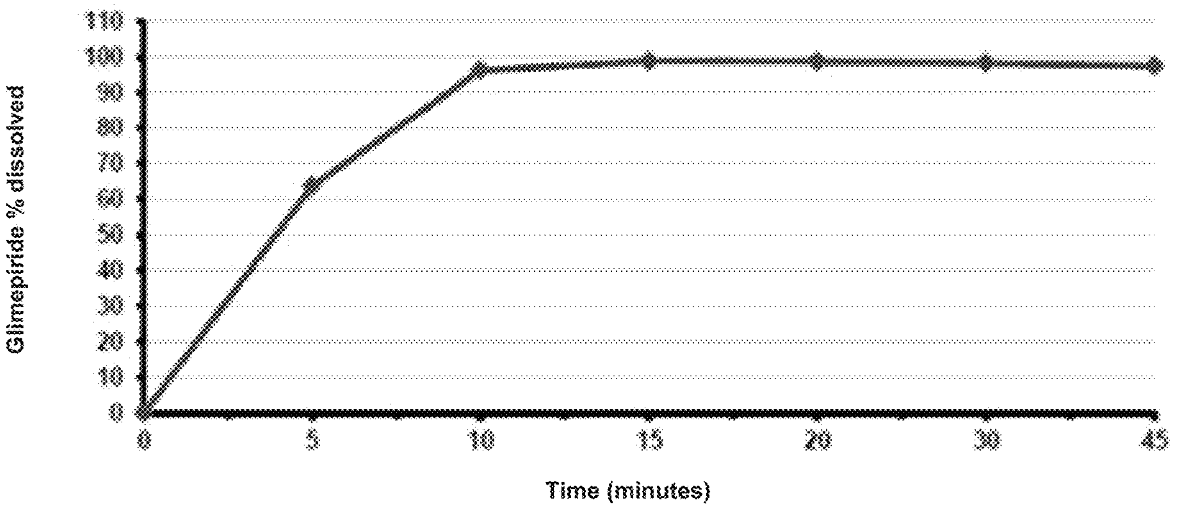
FIG. 4. Glimepiride dissolution profile of the combination drug comprising glimepiride 2 mg/vildagliptin 50 mg/metformin hydrochloride 1000 mg.
Figure 5:
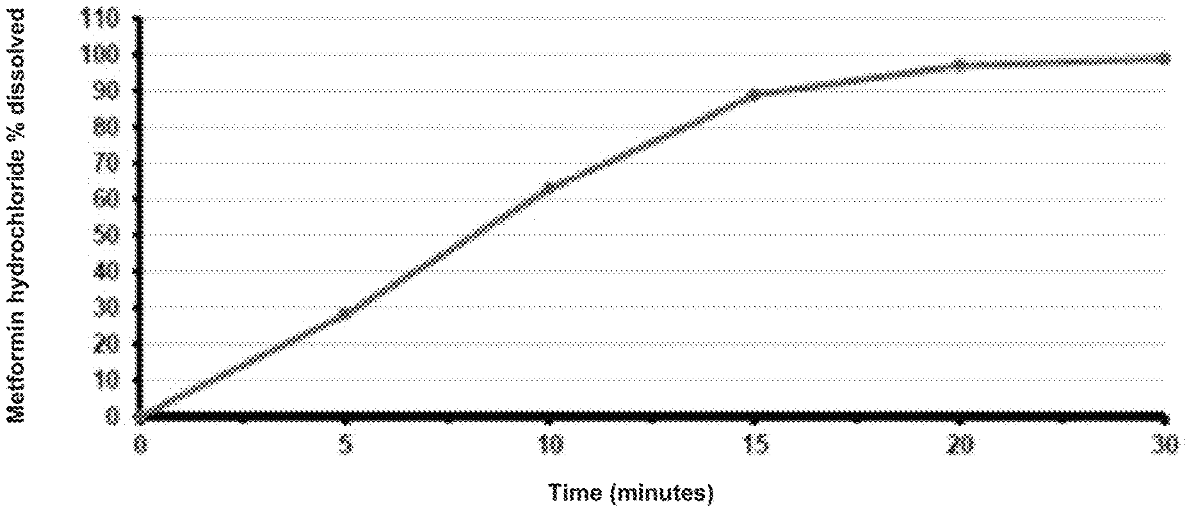
FIG. 5. Metformin dissolution profile of the combination drug comprising glimepiride 4 mg/vildagliptin 50 mg/metformin hydrochloride 1000 mg.
Figure 6:
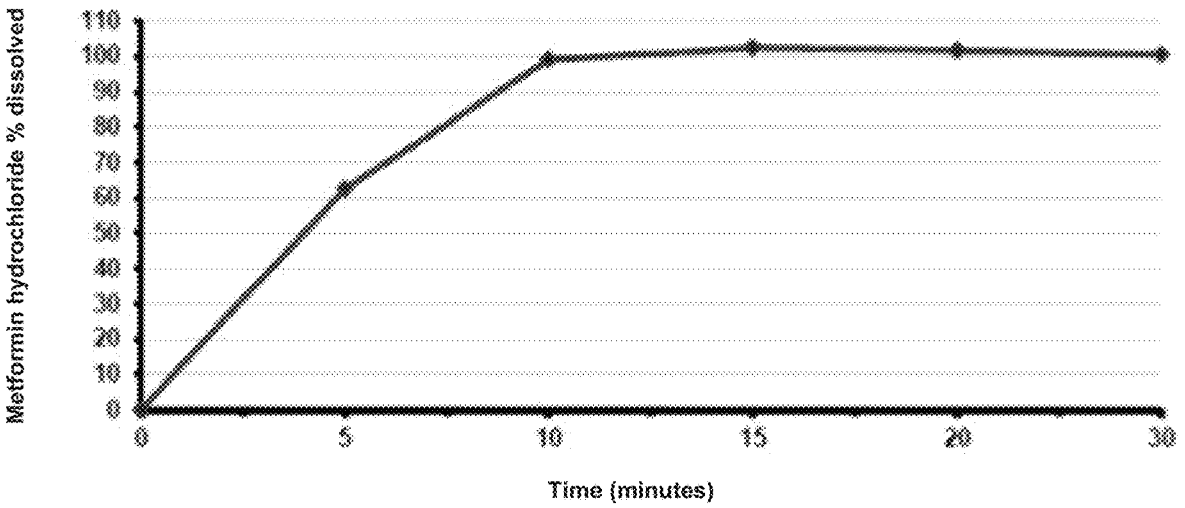
FIG. 6. Metformin dissolution profile of the combination drug comprising glimepiride 2 mg/vildagliptin 50 mg/metformin hydrochloride 1000 mg.

Pharmaceutically Acceptable Salt. In this invention, Pharmaceutically Acceptable Salt should be understood as a compound that retains the biological efficacy and properties of the given compound, and are not biologically, or otherwise, undesirable (P. Heinrich Stahl and Camille G. Wermuth (Eds.) Pharmaceutical Salts Properties, Selection, and Use (International Union of Pure and Applied Chemistry), Wiley-VCH; $2^{a}$ Revised Edition (May 16, 2011)). Pharmaceutically acceptable base addition salts can be prepared from inorganic or organic bases. Salts derived from inorganic bases include, by way of example only, sodium, potassium, lithium, ammonium, calcium, and magnesium salts. Salts derived from organic bases include, but are not limited to, salts of primary, secondary, and tertiary amines. Specific examples of suitable amines include isopropylamine, trimethylamine, diethylamine, tri (isopropyl) amine, tri (n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperidine, and the like.

Pharmaceutically acceptable acid addition salts can be prepared from inorganic or organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, maleic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

Excipient. In this invention, the term Excipient should be understood as the ingredient that is part of the present pharmaceutical composition. Excipients can be diluents, disintegrants, lubricants, coating, absorbents, among others.

Stability. It is the ability of a pharmaceutical product to retain its chemical, physical, microbiological, and biopharmaceutical properties within specified limits throughout its shelf life.

This invention is an innovative stable drug adapted to be of immediate release in a single dosage form for use in the treatment, better control, and management of diabetes Mellitus type 2, and at the same time, to solve a set of important technological challenges in the manufacture of said drug due to the physicochemical properties and the difference in dosage of the combination of the drugs it comprises to ensure obtaining a stable product for such purposes. Thus, a combination drug product is described characterized in that it comprises: (a) a sulfonylurea, (b) a dipeptidyl peptidase-4 (DPP4) inhibitor, and (c) a biguanide, or a pharmaceutical salt of any of the same, in pharmaceutically acceptable amounts in the range between 1-4 mg, 50 mg, and 500-1000 mg respectively, in combination with pharmaceutically acceptable excipients and/or vehicles.

In one embodiment of the invention, the sulfonylurea is found in a pharmaceutically acceptable amount of preferably 1 mg. In another embodiment of the invention, the sulfonylurea is found in a pharmaceutically acceptable amount of preferably 2 mg. In another preferable embodiment of the invention, the sulfonylurea is found in a pharmaceutically acceptable amount of 4 mg.

In another embodiment of the invention, the biguanide is found in a pharmaceutically acceptable amount of preferably 500 mg. In another embodiment of the invention, the biguanide is found in a pharmaceutically acceptable amount of preferably 1000 mg.

In a most preferable embodiment of the invention, the drug product combines in a single dosage form: (a) a sulfonylurea, (b) a dipeptidyl peptidase-4 (DPP4) inhibitor, and (c) a biguanide, or a pharmaceutical salt of any thereof, in pharmaceutically acceptable amounts of 1/50/500 mg respectively.

In an even more preferable embodiment of the invention, the drug product combines in a single dosage form: (a) a sulfonylurea, (b) a dipeptidyl peptidase-4 (DPP4) inhibitor, and (c) a biguanide, or a pharmaceutical salt of any thereof, in pharmaceutically acceptable amounts of 2/50/1000 mg respectively.

In a most preferable embodiment of the invention, the drug product combines in a single dosage form: (a) a sulfonylurea, (b) a dipeptidyl peptidase-4 (DPP4) inhibitor, and (c) a biguanide, or a pharmaceutical salt of any thereof, in pharmaceutically acceptable amounts of 4/50/1000 mg respectively.

Likewise, the fixed combination in a single dosage form of a sulfonylurea, a dipeptidyl peptidase-4 (DPP4) inhibitor, and a biguanide, is preferably glimepiride, vildagliptin and metformin, or a pharmaceutically acceptable salt of any of the same. Metformin, preferably, in its hydrochloride salt form.

The combination drug of this invention is further in a single solid dosage form, adapted to be of immediate release. The solid pharmaceutical form of the combination medicament is selected from the group comprising a tablet, caplet, granules, lozenges, pills. In one embodiment of the invention, the preferred solid dosage form is the tablet because of its dosage accuracy, plus being the best-accepted dosage form because of its easy administration. An alternative are capsules; however, it is not possible to dose such a high concentration of drugs due to the limited size of the capsules. In the case of tablets, it is possible to reduce the volume of the powders and thus facilitate their handling and administration.

Tablets designed in caplet form also facilitate swallowing and present the smallest possible size for the amount and weight of the tablets. In one embodiment, the design features a groove.

In this regard, this invention also relates to the use of (a) a sulfonylurea, (b) a dipeptidyl peptidase-4 (DPP4) inhibitor, and (c) a biguanide, or a pharmaceutical salt of any of the same, in pharmaceutically acceptable amounts in the range between 1-4 mg, 50 mg, and 500-1000 mg respectively, in combination with pharmaceutically acceptable excipients and/or vehicles for the manufacture of a drug product useful for the treatment, control, and management of type 2 diabetes mellitus in individuals requiring triple oral therapy, and wherein the sulfonylurea, the dipeptidyl peptidase-4 (DPP4) inhibitor, and the biguanide is preferably glimepiride, vildagliptin, and metformin, or a pharmaceutically acceptable salt of any thereof. Metformin, preferably, in its hydrochloride salt form. The method makes it possible to obtain a drug product easy to administer in a single dose.

In one embodiment of the invention, the sulfonylurea, the dipeptidyl peptidase-4 (DPP4) inhibitor, and the biguanide, or a pharmaceutical salt of any of the same, are preferably in pharmaceutically acceptable amounts of 1/50/500 mg, more preferably 2/50/1000 mg, and most preferably 4/50/1000 mg respectively, in combination with pharmaceutically acceptable excipients and/or vehicles.

The combination of (a) a sulfonylurea, (b) a dipeptidyl peptidase-4 (DPP4) inhibitor, and (c) a biguanide, or a pharmaceutical salt of either, in pharmaceutically acceptable amounts represents a set of significant technological challenges due to the physicochemical properties of the drugs. The technological complexity lies in the fact that when these three drugs are present, one of them is sensitive to humidity and light in a dispensing medium in which the absorption of these drugs is not affected, with light protection coating without affecting the release of the drugs. On the other hand, the proper selection of excipients and manufacturing conditions, as well as the difference in doses to ensure obtaining a stable product in the development of the drug formulation, play a very important role in relation to the release of drugs and the speed of absorption in the body.

The process lies in the selection of the unitary operations, the order, and the execution time to control the different physicochemical properties of the drugs, so the critical operations of the manufacturing process are described below: Mix 1 is necessary to improve the technological properties of the drugs with the granulation materials; while Mix 2 is necessary to protect the drug with the adsorbent. Sieving is essential since it is required to homogenize the particle size of the drugs and materials placed in these steps, and they must be uniform. Coating is necessary and must be carried out at a temperature range of 40-55° C. to avoid a very long contact of water with the active ingredients and thus obtain a barrier against light and humidity. Preferably, the temperature interval is 45-50° C., specifically 45-47° C.

A series of tests were carried out in which the components of the formulation were selected on the basis of their function, and their concentration was established in relation to the behavior of the product ensuring the proper functioning of the drug product, in which the absence or modification of one of them does not comply with the established quality characteristics.

The pharmaceutical composition of this invention comprises pharmaceutically acceptable excipients and/or vehicles including, but not limited to, binders, diluents, disintegrants, lubricants, solvents and/or solubilizers, adsorbents, and coatings.

Examples of pharmaceutically acceptable diluents, whose function known in the prior state of the art include adjusting and maintaining constant tablet weight, compaction and flow, include, but are not limited to, cellulose derivatives such as microcrystalline cellulose, phosphate derivatives such as dibasic calcium phosphate, starch derivatives such as pregelatinized starch and corn starch, as well as mannitol, xylitol, maltitol, lactitol, sorbitol, sucrose or combinations thereof. In one embodiment, the diluent is preferably microcrystalline cellulose, preferably microcrystalline cellulose PH 101 in a pharmaceutically acceptable amount in the range of 5-90%, preferably in a concentration of 5-10%; more preferably in an amount of 6-8%.

Pharmaceutically acceptable disintegrants include, but are not limited to, croscarmellose, cellulose derivatives such as hydroxypropyl cellulose, carboxymethyl cellulose, microcrystalline cellulose, povidone derivatives such as crospovidone, starch derivatives such as pregelatinized starch, sodium starch glycolate, and corn starch. In one embodiment, the disintegrant is preferably crospovidone, which is selected in this invention for its high capacity to rapidly uptake water and increase its volume providing a shorter disintegration time with respect to other materials, in a pharmaceutically acceptable amount in the range of 0.5-15%, preferably 0.5-5%, more preferably 4-5%.

Pharmaceutically acceptable adsorbents include, but are not limited to, aluminum derivatives (aluminum hydroxide, aluminum oxide, aluminum phosphate), clays or earths (atalpugite, betonite, hectorite, kaolin, pectin), silica derivatives (calcium silicate, colloidal silicon dioxide, aluminum magnesium silicate), cellulose derivatives (microcrystalline cellulose, cellulose), magnesium derivatives (magnesium carbonate, magnesium silicate), and magnesium aluminum metasilicate due to their ability to adsorb residual water in the solid pharmaceutical form or captured through the environment to improve drug stability. In one embodiment, the adsorbent is preferably aluminum magnesium metasilicate in a pharmaceutically acceptable amount in the range of 0.5 to 90%, preferably, 0.5-1%.

Examples of pharmaceutically acceptable binders include, but are not limited to, cellulose derivatives (hydroxypropylcellulose, carboxymethylcellulose), hydrogenated vegetable oil derivatives, ethylene glycol derivatives (peg-300, peg-3000), gum derivatives (acacia gum), agar, alginate derivatives (alginic acid), calcium derivatives (calcium carbonate, calcium phosphate), carbomers, chitosan, povidone derivatives (copovidone, cropovidone). In one embodiment, the binder is preferably polyvidone K90 which is selected in this invention because it generates, in contact with water and other materials, an optimum granule for the compression stage, improving flow and increasing the density of the materials. It is in a pharmaceutically acceptable amount in the range of 0.5 to 5%, more preferably in the range of 0.5 to 5% and most preferably from 2-4%.

Examples of pharmaceutically acceptable solubilizers include, but are not limited to, polyethylene glycol derivatives (polyoxyethyl alkyl ether, hydrogenated castor oil), sodium lauryl sulfate, sorbitan esters, and benzalkonium chloride. In one embodiment, the binder is preferably poloxamer 188, which is selected in this invention because of the low solubility of glimepiride retarding the solvation rate of the three drugs, and which is in a pharmaceutically acceptable amount in the range of 0.01 to 5%, more preferably in the range of 0.01 to 2%.

Examples of pharmaceutically acceptable lubricants include, but are not limited to, magnesium stearate, zinc stearate, calcium stearate, stearic acid, monostearate, stearyl fumarate; talc, and sulfated derivatives such as magnesium lauryl sulfate. The lubricant allows preventing sticking between the different toolings during the compression process of the solid dosage form. In one embodiment, the lubricant is preferably magnesium stearate in a pharmaceutically acceptable amount in the range of 0.25 to 10%, more preferably 0.25-1%.

On the other hand, the composition of this invention may contain coatings, which may be in an enunciative and non-limiting manner selected from cellulose derivatives such as hydroxypropylmethyl cellulose, hydroxypropyl cellulose, carboxymethyl celluloses; polyvinyl derivatives such as polyvinyl alcohol; polyethylene glycol, povidones in all grades K and their derivatives, as well as moisture barrier coatings. In one embodiment, the moisture and light barrier coating is preferably Opadry, such as Opadry AMB II in a pharmaceutically acceptable amount in the range of 0.5 to 6%, more preferably in the range of 1 to 4%, most preferably from 3 to 4%.

The composition of this invention also comprises solvent, such as and preferably water in a pharmaceutically acceptable or enough amount (q.s.).

Having evaluated and defined the drug formulation and process as described above, the drug formulation comprises the following components according to Table 1:

TABLE 1

Components in the drug formulation

| Components | Function |
| --- | --- |
| Glimepiride | Drug 1 |
| Vildagliptin | Drug 2 |
| Metformin Hydrochloride | Drug 3 |
| Microcrystalline cellulose PH 101 | Diluent |
| Polyvidone K90 | Binder |
| Poloxamer 188 | Solubilizer |
| Aluminium magnesium metasilicate | Adsorbent |
| Crospovidone | Disintegrant |
| Magnesium stearate | Lubricant |
| Opadry AMB II | Moisture barrier |
| Purified water (mL) | Solvent |

Due to the innovation made in the process and formulation of the drug, it was possible to obtain a product with proven stability through studies in accordance with current regulations in which the quality attributes were met during the evaluation period. Stability tests are a means to compare different formulations, packaging materials, or manufacturing processes in short-term experiments. As soon as the final formulation and manufacturing process are established, the manufacturer conducts a series of stability tests that will predict the stability of the product or drug, in this case, and determine its shelf life and storage conditions.

The initial results for the determination of drug formulation stability at the condition of 40° C./75% RH are shown below (Table 2), where the drug formulations are presented in doses of 1/50/500 mg, 2/50/1000 mg, and 4/50/1000 mg for sulfonylurea, dipeptidyl peptidase-4 (DPP4) inhibitor, and biguanide respectively:

TABLE 2

Initial stability data (time zero)

| | | Initial result | | |
| --- | --- | --- | --- | --- |
| Determination | Specification | Lot 1 (dosage 1/50/ 500 mg) | Lot 2 (dosage 2/50/ 1000 mg) | Lot 3 (dosage 4/50/ 1000 mg) |
| Glimepiride Content | 90-110% | 98.30 | 98.40 | 95.60 |
| Vildagliptin Content | 90-110% | 98.80 | 97.70 | 94.00 |
| Metformin HCl Content | 90-110% | 99.50 | 99.50 | 99.00 |
| Glimepiride Dissolution | Q = 70% in 60 minutes | 96.70 | 94.90 | 98.30 |
| Vildagliptin Dissolution | Q = 70% in 30 minutes | 97.70 | 97.90 | 99.52 |
| Metformin HCl Dissolution | Q = 70% in 60 minutes | 100.54 | 100.20 | 100.88 |

The results at 6 months in the 40° C./75% RH condition are shown below (Table 3), where the drug formulations are presented in doses of 1/50/500 mg, 2/50/1000 mg, and 4/50/1000 mg for sulfonylurea, dipeptidyl peptidase-4 (DPP4) inhibitor, and biguanide respectively.

TABLE 3

| Stability data at 6 months | | | | |
|---|---|---|---|---|
| | | Result | | |
| Determination | Specification | Lot 1 (dosage 1/50/ 500 mg) | Lot 2 (dosage 2/50/ 1000 mg) | Lot 3 (dosage 4/50/ 1000 mg) |
| Glimepiride Content | 90-110% | 94.2 | 94.1 | 96.7 |
| Vildagliptin Content | 90-110% | 98.2 | 99.3 | 98.3 |
| Metformin HCl Content | 90-110% | 99.7 | 100.5 | 100.27 |
| Glimepiride Dissolution | Q = 70% in 60 min | 95.4 | 91.6 | 102.66 |
| Vildagliptin Dissolution | Q = 70% in 30 min | 101.1 | 97.9 | 96.35 |
| Metformin HCl Dissolution | Q = 70% in 60 min | 98.9 | 102.3 | 100.63 |

In another embodiment of the invention, bioavailability tests are performed to determine whether there are differences in the magnitude and rate of absorption between the test product of this invention (fixed dose combination) and co-administration of reference drugs that impact the bioavailability of the drugs upon administration.

After co-administration of the reference drugs A: Glimetal® tablets with 4 mg glimepiride/1000 mg metformin hydrochloride, lot 19C105V2 manufactured by Laboratorios Silanes S.A. de C.V., and the reference drug of vildagliptin indicated by the COFEPRIS, the results of the study show no statistically significant differences for the $C_{max}$ and $ABC_{0-t}$ parameters of metformin and vildagliptin. However, with the intention of reducing the risk of acute hypoglycemia, the comparative analysis of glimepiride shows no differences in the amount absorbed ($ABC_{0-t}$) but does show differences in the rate of absorption ($C_{max}$) considering the intervals 80-125% (see Example 6).

The person skilled in the art will find that multiple variations and modalities are possible in the realization of this invention without departing from the spirit and scope of this invention to ensure the proper functioning of the product and to meet the required quality characteristics.

EXAMPLES

Example 1. Manufacturing Process for the Combination Drug in Tablet Form

1. Sieve 35% diluent, Drug 1, Drug 3, solubilizer, binder, and 60% disintegrant, and mix (Mix 1) for 1.6 minutes (Sieve 1).
2. Sieve Drug 2, 40% disintegrant, 65% diluent, and adsorbent, and mix (Mix 2) for 3 minutes (Sieve 2).
3. Wet and granulate Sieve 1 for 1.6 minutes with 44% of the purified water.
4. Dry the granulate to a moisture content of 1.5-2.5% w/w (Granulate 1).
5. Sieve Granulate 1 (Sieve 3).
6. Mix Sieve 2 and Sieve 3 for 3 minutes (Mix 3).
7. Sieve the lubricant and mix with the powder of Mix 3 for 5 minutes.
8. Compress according to specifications.
9. Mix the solvent and the moisture barrier for 45 minutes.
10. Recoat with a temperature range of not less than 40° C. and not more than 55° C., preferably in the range of 45°-50° C., more preferably between 45-47° C., with the above system according to specifications.

Example 2. Qualitative and Quantitative Formulation of the Combination Drug

TABLE 4

| Components in the drug formulation | | |
|---|---|---|
| Components | mg/Tab | Function |
| Glimepiride | 1.00 | Drug 1 |
| Vildagliptin | 50.00 | Drug 2 |
| Metformin Hydrochloride | 500.00 | Drug 3 |
| Microcrystalline cellulose PH 101 | 44.90 | Diluent |
| Polyvidone K90 | 19.30 | Binder |
| Poloxamer 188 | 0.60 | Solubilizer |
| Aluminum magnesium metasilicate | 5.00 | Adsorbent |
| Crospovidone | 30.00 | Disintegrant |
| Magnesium stearate | 3.20 | Lubricant |
| Opadry AMB II white 88A180021 | 21.00 | Moisture barrier |
| Purified water (mL) | q.s. | Solvent |

Example 3. Qualitative and Quantitative Formulation of the Combination Drug

TABLE 5

| Components in the drug formulation | | |
|---|---|---|
| Components | mg/Tab | Function |
| Glimepiride | 2.00 | Drug 1 |
| Vildagliptin | 50.00 | Drug 2 |
| Metformin Hydrochloride | 1000.00 | Drug 3 |
| Microcrystalline cellulose PH 101 | 103.0 | Diluent |
| Polyvidone K90 | 43.0 | Binder |
| Poloxamer 188 | 1.00 | Solubilizer |
| Aluminum magnesium metasilicate | 5.00 | Adsorbent |
| Crospovidone | 60.00 | Disintegrant |
| Magnesium stearate | 6.00 | Lubricant |
| Opadry AMB II white 88A180021 | 40.00 | Moisture barrier |
| Purified water (mL) | q.s. | Solvent |

Example 4. Qualitative and Quantitative Formulation of the Combination Drug

TABLE 6

| Components in the drug formulation | | |
|---|---|---|
| Components | mg/Tab | Function |
| Glimepiride | 4.00 | Drug 1 |
| Vildagliptin | 50.00 | Drug 2 |
| Metformin Hydrochloride | 1000.00 | Drug 3 |
| Microcrystalline cellulose PH 101 | 100.0 | Diluent |
| Polyvidone K90 | 43.0 | Binder |
| Poloxamer 188 | 2.00 | Solubilizer |
| Aluminum magnesium metasilicate | 5.00 | Adsorbent |
| Crospovidone | 60.00 | Disintegrant |
| Magnesium stearate | 6.00 | Lubricant |
| Opadry AMB II white 88A180021 | 40.00 | Moisture barrier |
| Purified water (mL) | q.s. | Solvent |

Example 5. Content and Dissolution Test

The person skilled in the art may notice that several methodologies for content testing exist in the state of the art, such as in Pharmacopoeias: FEUM, USP, British Pharmacopoeia, pharmaceutical norms and standards, so it will be evident for a technician in the field to follow or combine the cited existing pharmaceutical reference documents to solve and perform this methodology, where multiple variations are possible in performing this test without departing from the spirit and scope of the same to ensure the proper functioning of the product and meet the required quality characteristics.

The person skilled in the art may also notice that several methodologies for the dissolution test exist in the state of the art, such as in Pharmacopoeias: FEUM, USP, British Pharmacopoeia, pharmaceutical norms and standards, so it will be evident for a technician in the field to follow or combine the cited existing pharmaceutical reference documents to solve and perform this methodology, where multiple variations are possible in the performance of this test without departing from the spirit and scope of the same to ensure the proper functioning of the product and meet the required quality characteristics.

On the other hand, the dissolution test (in vitro test) serves to determine the rate (amount/time) and extent (total amount) at which a drug is released from the dosage form; in the case of the dissolution profile, it corresponds to the quantification at different times of the dissolved drug under standardized conditions. The importance of the dissolution test lies in the following:

a) It is a guide for the development of new formulations during product development: it allows evaluating the possible interference of excipients or the manufacturing process on drug release.
b) Process control and quality assurance: it helps to ensure the continuous quality of the product and its optimization after a change in manufacturing, formulation, manufacturing site, and process scale-up.
c) In vivo development indicator: it is an indicator of bioavailability; it allows establishing the correlation between in vitro parameters with bioavailability results.

Thus, the dissolution tests of this invention were implemented as described in the FEUM 12th edition (2018) and internationally recognized scientific literature available and subsequently validated; one method to quantify glimepiride, another to quantify vildagliptin, and a third method to quantify metformin hydrochloride. The results showed that the methods are precise, accurate, linear, and selective.

Dissolution profiling was performed for combination drugs comprising:

- glimepiride 2 mg/vildagliptin 50 mg/metformin hydrochloride 1000 mg (tablets), lot DFF1901-24. This drug has a titer for glimepiride of 95.7% (3.8 mg/tablet); for vildagliptin of 96.5% (48.3 mg/tablet); and for metformin of 97.9% (979.0 mg/tablet).
- glimepiride 4 mg/vildagliptin 50 mg/metformin hydrochloride 1000 mg (tablets), lot 19F081G1. This drug has a titer for glimepiride of 97.1% (1.9 mg/tablet); for vildagliptin of 99.9% (50.0 mg/tablet); and for metformin of 98.6% (986.0 mg/tablet).

Dissolution Profile of Vildagliptin, Glimepiride, Metformin

Dissolution profile testing was performed in duplicate for a total of 12 dosage units of each drug composition: glimepiride 2 mg/vildagliptin 50 mg/metformin hydrochloride 1000 mg; and glimepiride 4 mg/vildagliptin 50 mg/metformin hydrochloride 1000 mg. An Agilent Technologies dissolver, a dissolution medium temperature 37° C.±0.5° C. for a dissolution medium volume 900 mL±1% (9 mL) (except for metformin), and manual sampling type for a sampling volume of 10 mL were used. While for the results a calibration curve was constructed using as mathematical model a least squares linear regression without including zero y=mx+b where:

- "y" is the analytical response (area of Vildagliptin, Glimepiride or Metformin hydrochloride),
- "x" is the added concentration of Vildagliptin, Glimepiride or Metformin hydrochloride,
- b=Ordinate to the origin of the calibration curve obtained from the regression,
- m=Slope of the calibration curve obtained from the regression.

Vildagliptin Dissolution Conditions
- Dissolution Apparatus 2 (paddles)
- Dissolution medium Water
- Stirring speed 75 rpm±2 rpm
- Sampling times 5, 10, 15, 15, 20, 30 min.±2%.

Vildagliptin Chromatographic Conditions
- HPLC AGILENT 1200
- UV wavelength 210 nm
- Analytical column ZORBAX SB-C18 2.1×100 3.5 μm
- Mobile phase 0.02 M potassium monobasic phosphate/Acetonitrile (90:10)
- Flow rate 0.3 mL/min
- Column temperature 45° C.
- Run time 4 minutes
- Injection volume 40 μL Glimepiride Dissolution Conditions
- Dissolution Apparatus 2 (paddles)
- Dissolution Medium Phosphate buffer pH 7.8
- Stirring speed 75 rpm±3 rpm
- Sampling times 5, 10, 15, 15, 20, 30 and 45 min.±2%.

Glimepiride Chromatographic Conditions
- HPLC AGILENT 1200
- UV wavelength 228 nm
- Analytical column KINETEX C18 2.1×100 5.0 μm
- Mobile phase Formic acid 0.2%/Acetonitrile: MEOH (40:30:30)
- Flow rate 0.5 mL/min
- Column temperature 40° C.
- Run time 4 minutes
- Injection volume 50 μL Metformin Dissolution Conditions
- Dissolution Apparatus 1 (baskets).
- Dissolution Medium Monobasic potassium phosphate 0.68% m/v pH: 6.8±0.1
- Volume of the Dissolution Medium 1000 mL±1% (10 mL)
- Stirring speed 100 rpm±3 rpm
- Sampling times 5, 10, 15, 20, and 30 min.±2%.

Metformin Chromatographic Conditions
- HPLC AGILENT 1200
- UV wavelength 233 nm
- ZORBAX SB-C18 column 2.1×100 mm and 3.5 μm particles
- Mobile phase Potassium monobasic phosphate 0.02 M (Methanol-Acetonitrile 50:50) 80:20
- Flow rate 0.3 mL/min
- Column temperature 45° C.
- Run time 3 minutes
- Injection volume 5 μL The individual results obtained from the dissolution profile test for the combination drugs are shown below. Tables 7-12 show the percentages dissolved in each beaker at the sampling times performed and the plot of the average percentages dissolved as a function of sampling times.

TABLE 7

Vildagliptin % dissolved - combination drug comprising glimepiride 4 mg/vildagliptin 50 mg/metformin hydrochloride 1000 mg.

| | Time (minutes) | | | | |
|---|---|---|---|---|---|
| CUP | 5 | 10 | 15 | 20 | 30 |
| 1 | 38.22 | 67.28 | 88.46 | 90.86 | 88.49 |
| 2 | 31.86 | 65.30 | 84.69 | 88.45 | 90.57 |
| 3 | 34.31 | 70.09 | 90.30 | 91.61 | 91.90 |
| 4 | 29.45 | 62.91 | 84.23 | 92.11 | 91.35 |
| 5 | 32.71 | 62.97 | 85.61 | 89.11 | 87.70 |
| 6 | 32.69 | 6379 | 85.17 | 88.96 | 88.17 |
| 7 | 41.32 | 75.04 | 87.56 | 86.85 | 87.37 |
| 8 | 40.05 | 69.03 | 92.17 | 91.64 | 90.10 |
| 9 | 33.37 | 70.47 | 90.47 | 90.94 | 91.17 |
| 10 | 35.97 | 71.41 | 90.48 | 91.57 | 89.59 |
| 11 | 34.05 | 70.44 | 82.95 | 82.65 | 80.42 |
| 12 | 38.13 | 69.18 | 86.88 | 88.91 | 88.04 |
| Average | 35.18 | 68.16 | 87.41 | 89.47 | 88.74 |
| Minimum | 29.45 | 62.91 | 82.95 | 82.65 | 80.42 |
| Maximum | 41.32 | 75.04 | 92.17 | 92.11 | 91.90 |
| CV % | 10.19 | 5.53 | 3.39 | 3.01 | 3.43 |

TABLE 8

Vildagliptin % dissolved - combination drug comprising glimepiride 2 mg/vildagliptin 50 mg/metformin hydrochloride 1000 mg.

| | Time (minutes) | | | | |
|---|---|---|---|---|---|
| CUP | 5 | 10 | 15 | 20 | 30 |
| 1 | 65.33 | 86.34 | 88.78 | 87.61 | 84.63 |
| 2 | 72.30 | 88.22 | 91.24 | 87.93 | 87.18 |
| 3 | 64.25 | 89.19 | 91.96 | 89.51 | 87.21 |
| 4 | 60.83 | 86.04 | 87.31 | 90.02 | 86.65 |
| 5 | 73.73 | 88.28 | 89.18 | 86.14 | 86.52 |
| 6 | 71.45 | 88.19 | 89.38 | 85.53 | 87.56 |
| 7 | 65.71 | 87.34 | 88.99 | 87.56 | 84.86 |
| 8 | 76.80 | 87.60 | 90.25 | 88.06 | 89.03 |
| 9 | 77.15 | 88.66 | 89.04 | 87.47 | 89.10 |
| 10 | 55.75 | 85.57 | 89.07 | 91.37 | 89.93 |
| 11 | 80.33 | 88.39 | 87.49 | 87.27 | 87.25 |
| 12 | 64.28 | 89.29 | 90.71 | 89.46 | 89.69 |
| Average | 68.99 | 87.76 | 89.45 | 88.16 | 87.47 |
| Minimum | 55.75 | 85.57 | 87.31 | 85.53 | 84.63 |
| Maximum | 80.33 | 89.29 | 91.96 | 91.37 | 89.93 |
| CV % | 10.76 | 1.38 | 1.55 | 1.88 | 1.97 |

TABLE 9

[]Glimepiride % dissolved-combination drug comprising glimepiride 4 mg/vildagliptin 50 mg/metformin hydrochloride 1000 mg

| | Time (minutes) | | | | | |
|---|---|---|---|---|---|---|
| CUP | 5 | 10 | 15 | 20 | 30 | 45 |
| 1 | 32.98 | 71.61 | 90.04 | 92.22 | 90.91 | 91.55 |
| 2 | 33.48 | 68.85 | 91.36 | 91.75 | 91.92 | 92.66 |
| 3 | 35.56 | 72.37 | 90.47 | 93.05 | 92.70 | 93.35 |
| 4 | 32.56 | 68.07 | 94.58 | 94.93 | 93.95 | 93.80 |
| 5 | 37.52 | 66.93 | 94.08 | 95.94 | 96.27 | 94.91 |
| 6 | 29.08 | 59.86 | 88.60 | 95.40 | 95.04 | 95.32 |
| 7 | 38.73 | 73.91 | 91.46 | 92.71 | 92.04 | 92.64 |
| 8 | 27.80 | 62.30 | 91.24 | 94.40 | 93.80 | 92.63 |
| 9 | 29.09 | 69.54 | 88.13 | 93.00 | 94.63 | 93.85 |
| 10 | 33.40 | 72.81 | 92.83 | 94.02 | 92.83 | 92.64 |
| 11 | 35.75 | 71.37 | 91.48 | 91.73 | 92.08 | 95.71 |
| 12 | 33.15 | 65.35 | 90.20 | 94.74 | 95.96 | 93.55 |
| Average | 33.26 | 68.58 | 91.21 | 93.66 | 93.51 | 93.55 |

TABLE 9-continued

[]Glimepiride % dissolved-combination drug comprising glimepiride 4 mg/vildagliptin 50 mg/metformin hydrochloride 1000 mg

| | Time (minutes) | | | | | |
|---|---|---|---|---|---|---|
| CUP | 5 | 10 | 15 | 20 | 30 | 45 |
| Minimum | 27.80 | 59.86 | 88.13 | 91.73 | 90.91 | 91.55 |
| Maximum | 38.73 | 73.91 | 94.58 | 95.94 | 96.27 | 95.71 |
| CV % | 10.13 | 6.33 | 2.13 | 1.54 | 1.83 | 1.33 |

TABLE 10

[]Glimepiride % dissolved-combination drug comprising glimepiride 2 mg/vildagliptin 50 mg/metformin hydrochloride 1000 mg

| | Time (minutes) | | | | | |
|---|---|---|---|---|---|---|
| CUP | 5 | 10 | 15 | 20 | 30 | 45 |
| 1 | 51.89 | 89.60 | 101.61 | 101.59 | 99.45 | 99.09 |
| 2 | 72.82 | 99.00 | 98.44 | 97.88 | 97.81 | 97.48 |
| 3 | 60.75 | 95.55 | 99.29 | 99.18 | 99.75 | 98.49 |
| 4 | 62.08 | 100.52 | 101.72 | 100.85 | 100.33 | 99.96 |
| 5 | 66.48 | 96.99 | 100.36 | 100.88 | 99.38 | 9885 |
| 6 | 74.94 | 95.39 | 97.81 | 99. 37 | 97.54 | 96.60 |
| 7 | 56.90 | 96.01 | 99.79 | 98.78 | 98.60 | 98.65 |
| 8 | 54.49 | 97.47 | 101.28 | 99.11 | 98.64 | 97.74 |
| 9 | 56.12 | 96.12 | 100.84 | 98.53 | 97.18 | 97.40 |
| 10 | 5149 | 93.39 | 99.61 | 98.17 | 98.45 | 96.16 |
| 11 | 80.93 | 103.70 | 99.20 | 97.69 | 97.69 | 98.53 |
| 12 | 76.89 | 93.12 | 95.20 | 94 03 | 96.38 | 92.79 |
| Average | 63.82 | 96.40 | 99.60 | 98.84 | 98.43 | 97.65 |
| Minimum | 51.49 | 89.60 | 95.20 | 94.03 | 96.38 | 92.79 |
| Maximum | 80.93 | 103.70 | 101.72 | 101.59 | 100.33 | 99.96 |
| CV % | 16.20 | 3.78 | 1.86 | 1.98 | 1.18 | 1.91 |

TABLE 11

Metformin % dissolved - combination drug comprising glimepiride 4 mg/vildagliptin 50 mg/metformin hydrochloride 1000 mg.

| | Time (minutes) | | | | |
|---|---|---|---|---|---|
| CUP | 5 | 10 | 15 | 20 | 30 |
| 1 | 25.36 | 60.01 | 83.83 | 100.60 | 101.29 |
| 2 | 33.86 | 64.17 | 99.26 | 101.68 | 98.89 |
| 3 | 34.05 | 70.99 | 97.66 | 104.64 | 100.73 |
| 4 | 30.55 | 72.92 | 99.89 | 96.96 | 103.02 |
| 5 | 34.01 | 67.65 | 100.95 | 100.62 | 105.51 |
| 6 | 34.31 | 6526 | 91.77 | 103.18 | 104.22 |
| 7 | 21.89 | 54.87 | 81.34 | 95.98 | 98.44 |
| 8 | 24.53 | 60.93 | 84.40 | 93.76 | 93.66 |
| 9 | 29.16 | 64.15 | 89.87 | 95.16 | 96.05 |
| 10 | 25.64 | 59.60 | 91.44 | 94.31 | 98.31 |
| 11 | 17.96 | 48.34 | 66.43 | 88.79 | 94.28 |
| 12 | 26.63 | 66.46 | 81.71 | 89.84 | 92.42 |
| Average | 28.16 | 62.94 | 89.05 | 97.13 | 98.90 |
| Minimum | 17.96 | 48.34 | 66.43 | 88.79 | 92.42 |
| Maximum | 34.31 | 72.92 | 100.95 | 104.64 | 105.51 |
| CV % | 19.13 | 10.81 | 11.36 | 5.24 | 4.29 |

TABLE 12

| Metformin % dissolved - combination drug comprising glimepiride 2 mg/vildagliptin 50 mg/metformin hydrochloride 1000 mg. | | | | | |
|---|---|---|---|---|---|
| | Time (minutes) | | | | |
| CUP | 5 | 10 | 15 | 20 | 30 |
| 1 | 66.01 | 100.39 | 100.95 | 100.95 | 98.99 |
| 2 | 77.13 | 101.08 | 103.31 | 99.64 | 99.60 |
| 3 | 49.98 | 89.86 | 107.40 | 105.70 | 102.79 |
| 4 | 62.26 | 99.21 | 103.64 | 102.09 | 100.74 |
| 5 | 60.00 | 98.61 | 101.75 | 101.29 | 10108 |
| 6 | 67.96 | 100.68 | 100.86 | 103.13 | 100.20 |
| 7 | 60.64 | 98.94 | 103.63 | 101.68 | 101.45 |
| 8 | 66.99 | 100.77 | 100.65 | 103.89 | 100.95 |
| 9 | 52.10 | 9529 | 100.39 | 101.25 | 100.91 |
| 10 | 53.81 | 100.97 | 103.46 | 102.22 | 99.27 |
| 11 | 62.93 | 103.24 | 98.35 | 101.24 | 101.49 |
| 12 | 71.81 | 100.15 | 104.31 | 96.56 | 98.95 |
| Average | 62.63 | 99.10 | 102.39 | 101.64 | 100.53 |
| Minimum | 49.98 | 89.86 | 98.35 | 96.56 | 98.95 |
| Maximum | 77.13 | 103.24 | 107.40 | 105.70 | 102.79 |
| CV % | 12.86 | 3.51 | 2.32 | 2.20 | 1.16 |

Comparison of Dissolution Profiles

Figure 7:
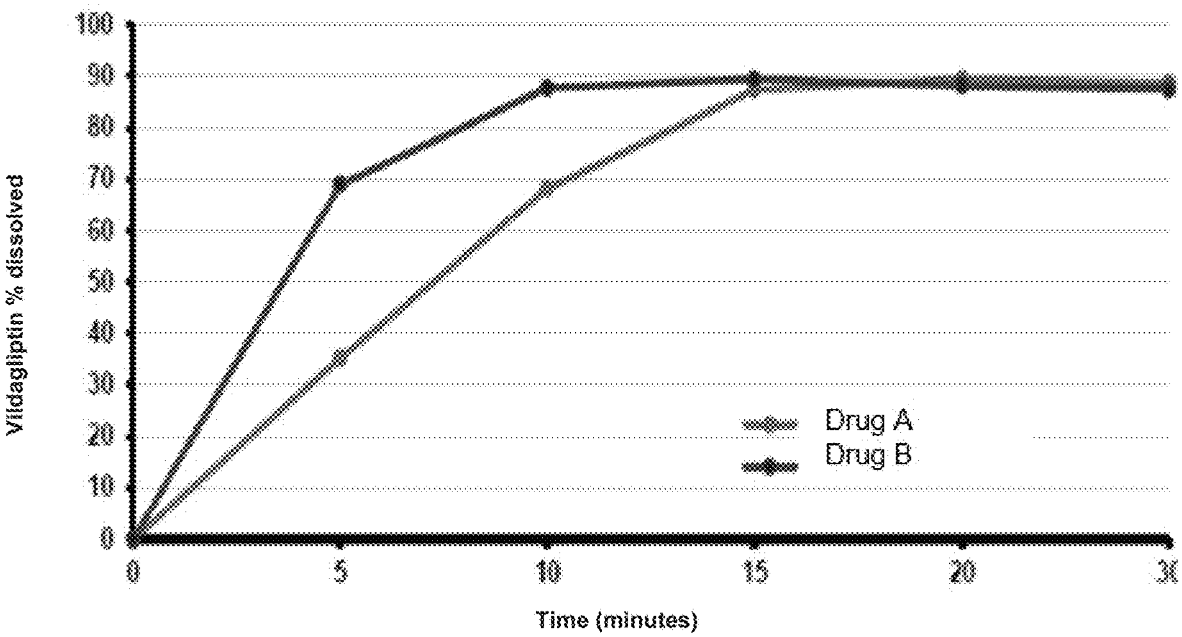
FIG. 7. Vildagliptin dissolution profile of the combination drug comprising glimepiride, vildagliptin, metformin hydrochloride.
Figure 8:
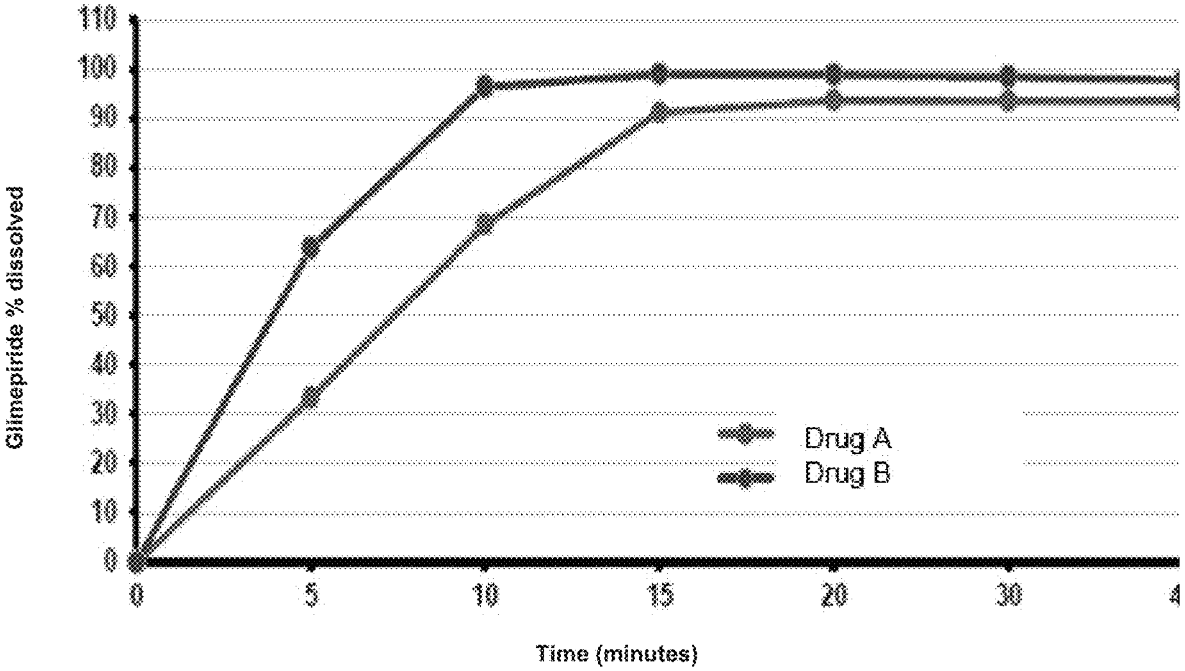
FIG. 8. Glimepiride dissolution profile of the combination drug comprising glimepiride, vildagliptin, metformin hydrochloride.
Figure 9:
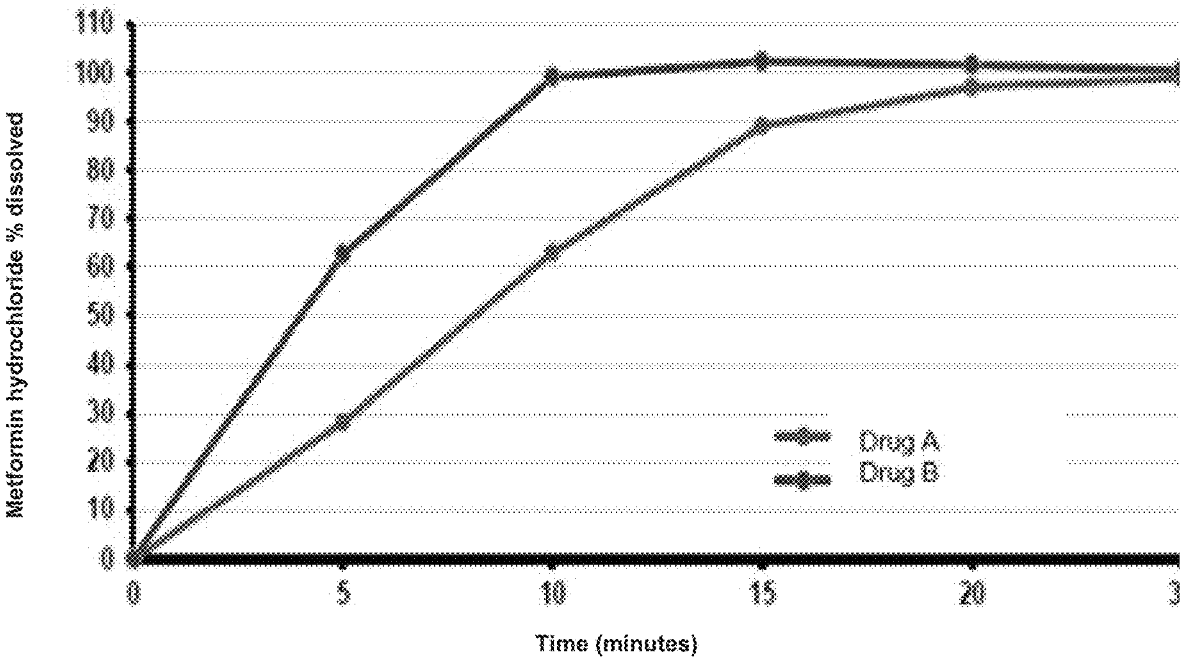
FIG. 9. Metformin dissolution profile of the combination drug comprising glimepiride, vildagliptin, metformin hydrochloride.
Figure 10:
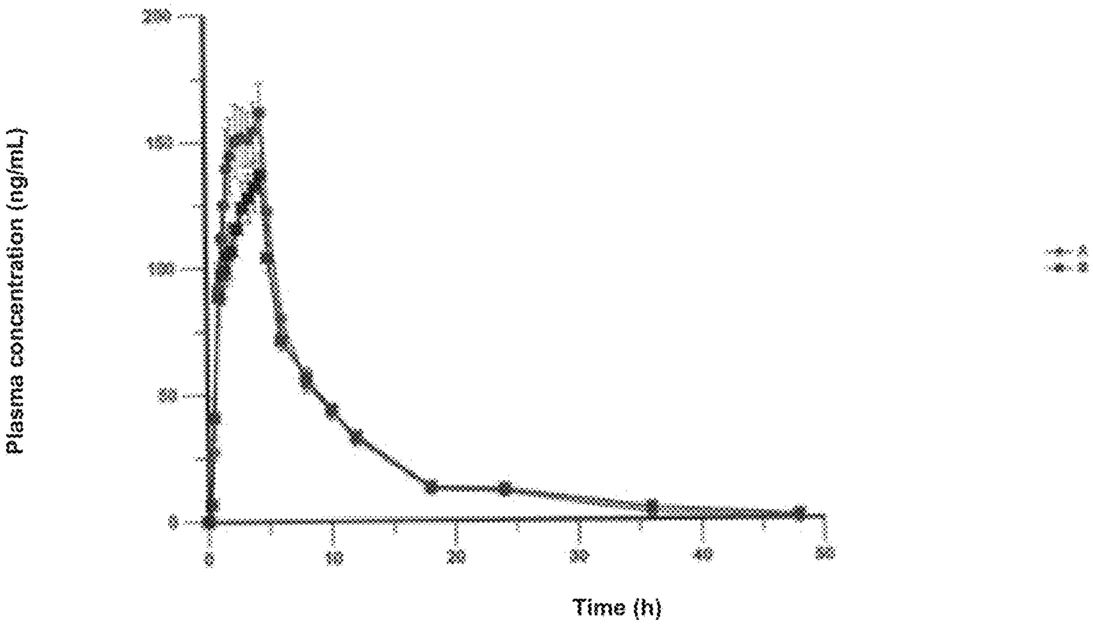
FIG. 10. Mean plasma concentration versus time. Mean pharmacokinetic profile of glimepiride±standard error on arithmetic scale (A: reference drug; B: test drug).
Figure 11:
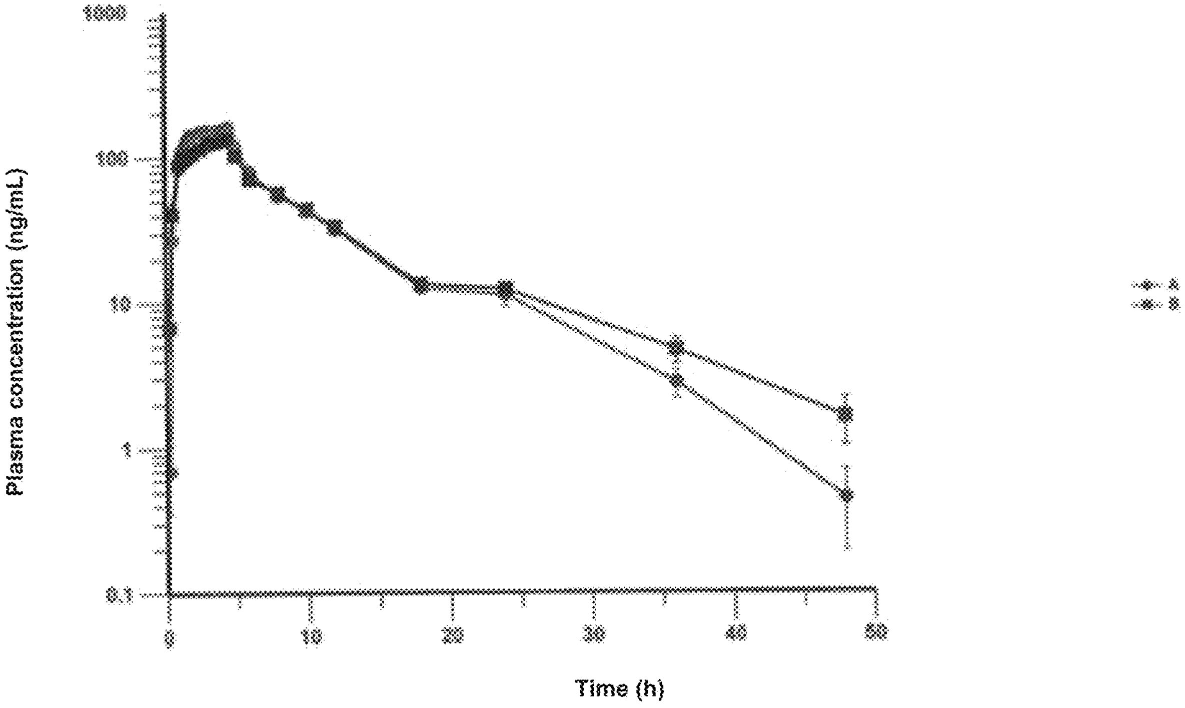
FIG. 11. Mean plasma concentration versus time. Mean pharmacokinetic profile of glimepiride±standard error on semilogarithmic scale (A: reference drug; B: test drug).
Figure 12:
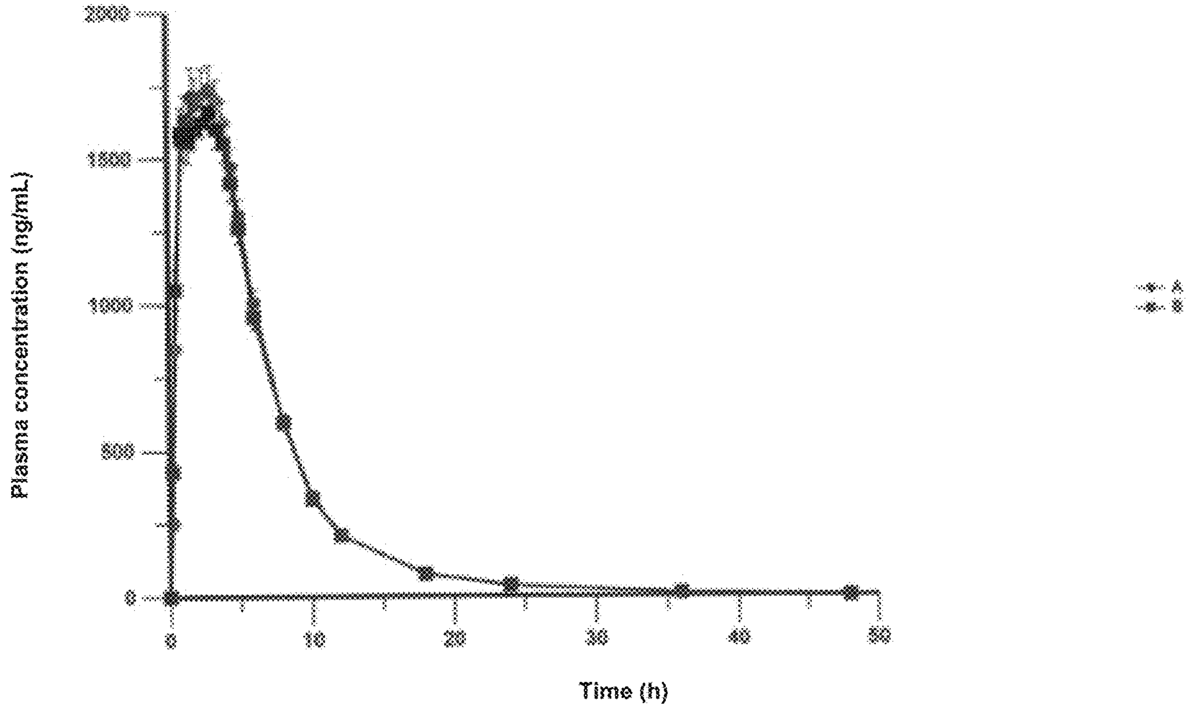
FIG. 12. Mean plasma concentration versus time. Mean pharmacokinetic profile of metformin±standard error on arithmetic scale (A: reference drug; B: test drug).
Figure 13:
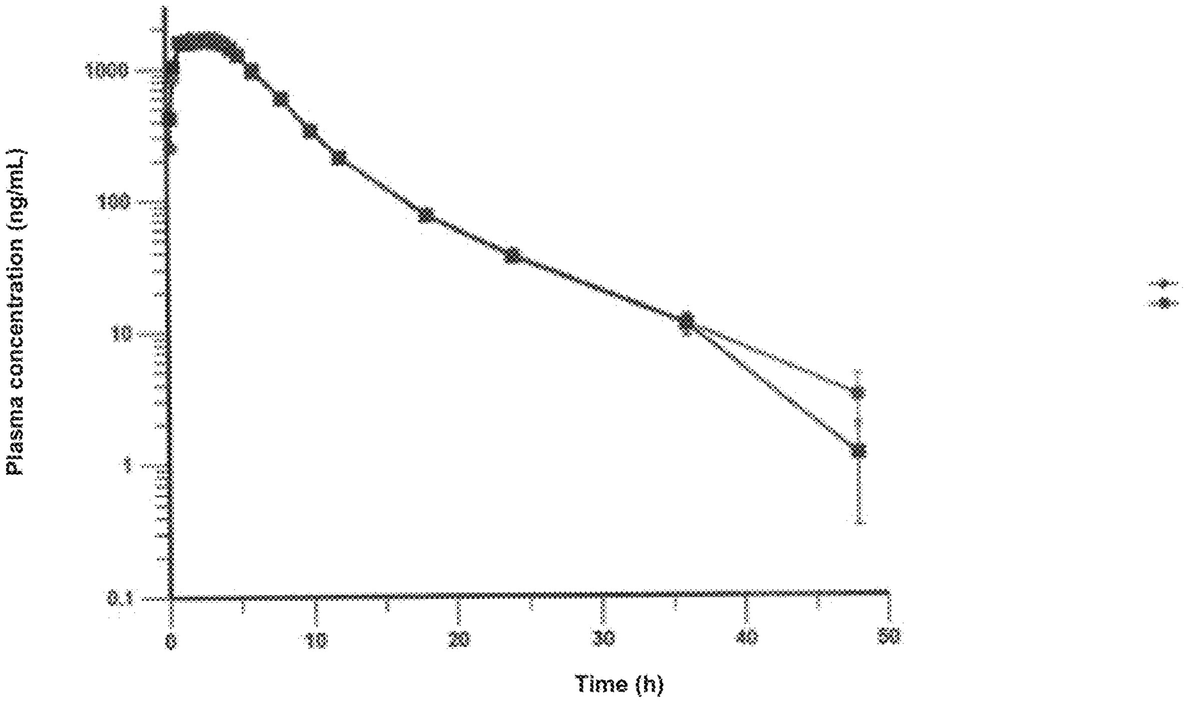
FIG. 13. Mean plasma concentration versus time. Mean pharmacokinetic profile of metformin±standard error on semilogarithmic scale (A: reference drug; B: test drug).
Figure 14:
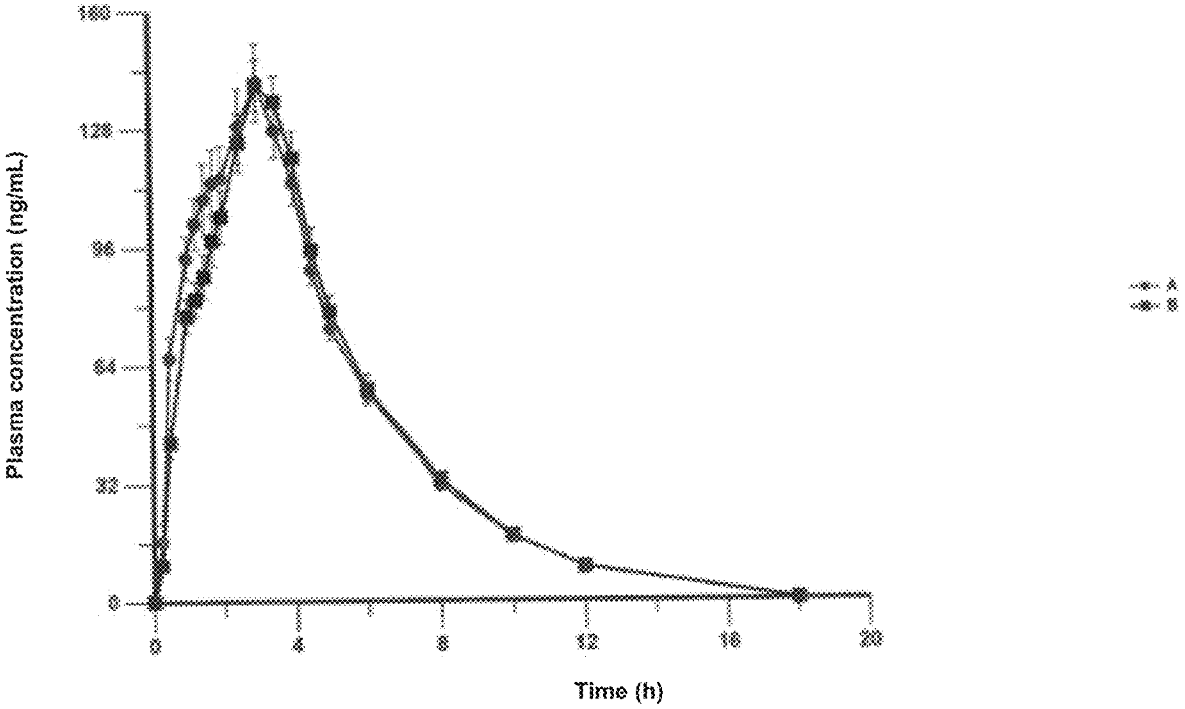
FIG. 14. Mean plasma concentration versus time. Mean pharmacokinetic profile of metformin±standard error on arithmetic scale (A: reference drug; B: test drug).
Figure 15:
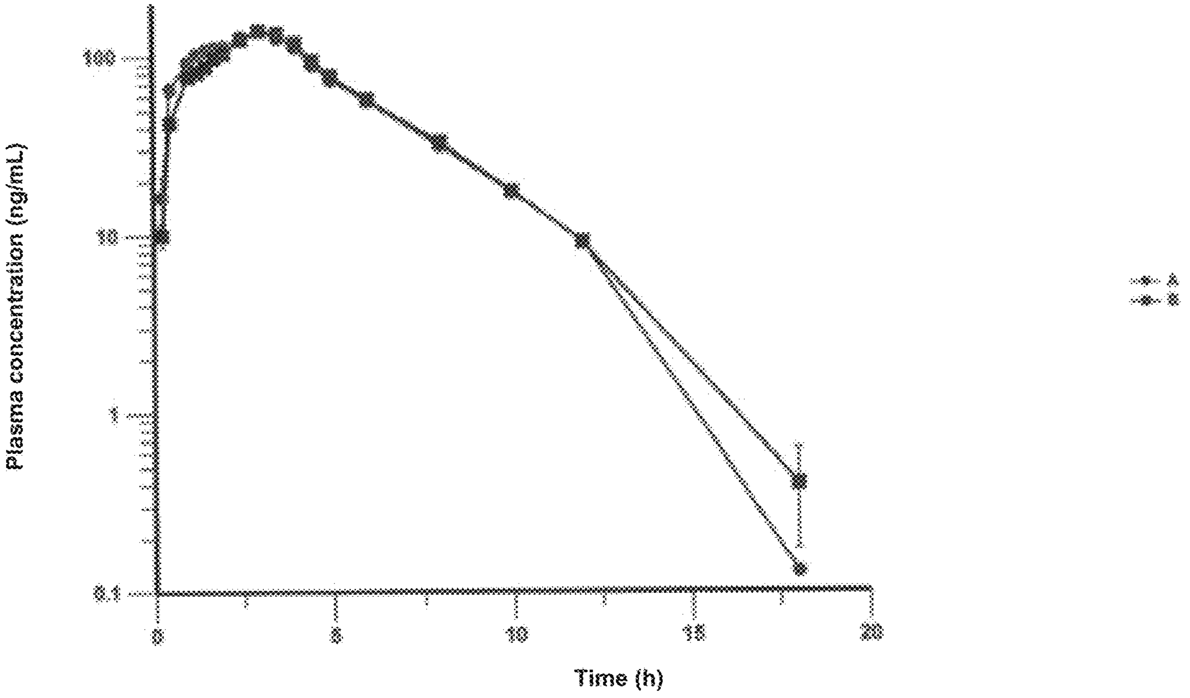
FIG. 15. Mean plasma concentration versus time. Mean pharmacokinetic profile of vildagliptin±standard error on semilogarithmic scale (A: reference drug; B: test drug).

Shown below as a comparative table (Tables 13-15) and graph (FIGS. 7-9) are the average dissolved percentages of each drug at the sampling times performed (the notation used "drug (A)" and "drug (B)" is different from that used in Example 6 for the bioavailability testing).

TABLE 13

| Dissolved percentage of vildagliptin | | |
|---|---|---|
| Time (min) | Combination drug (A) comprising glimepiride 4 mg/vildagliptin 50 mg/metformin hydrochloride 1000 mg | Combination drug (B) comprising glimepiride 2 mg/vildagliptin 50 mg/metformin hydrochloride 1000 mg hydrochloride 1000 mg |
| 0 | 0.00 | 0.00 |
| 5 | 35.18 | 68.99 |
| 10 | 68.16 | 87.76 |
| 14 | 87.41 | 89.45 |
| 20 | 89.47 | 88.16 |
| 30 | 88.74 | 84.47 |

TABLE 14

| Dissolved percentage of glimepiride | | |
|---|---|---|
| Time (min) | Combination drug (A) comprising glimepiride 4 mg/vildagliptin 50 mg/metformin hydrochloride 1000 mg | Combination drug (B) comprising glimepiride 2 mg/vildagliptin 50 mg/metformin hydrochloride 1000 mg hydrochloride 1000 mg |
| 0 | 0.00 | 0.00 |
| 5 | 33.26 | 63.82 |
| 10 | 68.58 | 96.40 |
| 15 | 91.21 | 99.60 |
| 20 | 93.66 | 98.84 |
| 30 | 93.51 | 98.43 |
| 45 | 93.55 | 94.65 |

TABLE 15

| Dissolved percentage of metformin hydrochloride | | |
|---|---|---|
| Time (min) | Combination drug (A) comprising glimepiride 4 mg/vildagliptin 50 mg/metformin hydrochloride 1000 mg | Combination drug (B) comprising glimepiride 2 mg/vildagliptin 50 mg/metformin hydrochloride 1000 mg hydrochloride 1000 mg |
| 0 | 0.00 | 0.00 |
| 5 | 28.16 | 62.63 |
| 10 | 62.94 | 99.10 |
| 15 | 89.05 | 102.39 |
| 20 | 97.13 | 101.64 |
| 30 | 98.90 | 100.53 |

In the graphical results, the analyzed drugs show certain similarity in their dissolution profiles since the combination drug comprising glimepiride 2 mg/vildagliptin 50 mg/metformin hydrochloride 1000 mg presents a more pronounced ascending phase than the combination drug comprising glimepiride 4 mg/vildagliptin 50 mg/metformin hydrochloride 1000 mg in the three drugs evaluated (Vildagliptin, Glimepiride and Metformin hydrochloride), which is confirmed by reviewing in the results tables the percentages dissolved at the sampling times performed. A low variability of the dissolved percentages is also observed in both drugs, in the three drugs evaluated (Vildagliptin, Glimepiride and Metformin hydrochloride), the CV % of the dissolved percentage was less than 20% at the first sampling time and less than 10% at the following sampling times (except for Metformin hydrochloride for the drug comprising glimepiride 4 mg/vildagliptin 50 mg/metformin hydrochloride 1000 mg).

The dissolution profile results for both drugs showed rapid dissolution of all three drugs evaluated, Vildagliptin, Glimepiride and Metformin hydrochloride, with dissolution percentages greater than 85% at 15 minutes; therefore, the dissolution profiles are considered similar, and the products can be classified as very fast dissolving.

Example 6. Bioavailability Testing

Algorithm 1 "Treatment Schemes in Diabetes Mellitus Type 2 (DM2)", included in the Clinical Practice Guideline Treatment of Diabetes Mellitus Type 2 in the first level of care, published by CENETEC, states that in the event of inadequate glycemic control (HbA1c >7% and ABG >130), dual oral therapy plus sulfonylurea should be initiated as one of the options. Additionally, the ADA (American Diabetes Association: Standards of medical care in Diabetes—2019) indicates that under inadequate glycemic control with metformin as first-line treatment, an iDPP4 can be added, and if despite the dual scheme there is no control, a sulfonylurea may be added. Likewise, when cost is an issue to be considered, metformin should be started, if there is no control, a sulfonylurea can be added, and if the therapeutic goal is not reached, an iDPP4 can be included.

On the other hand, the determination of the pharmacokinetic parameters of $C_{max}$ and area under the plasma concentration curve with respect to time ($ABC_{0-t}$) are determined, which allow characterizing the bioavailability of the drug of this invention from its dosage form, in terms of speed and degree of respective absorption. Therefore, the purpose of the bioavailability tests is to determine if there are differences in the magnitude and speed of absorption between the test product of the present invention (fixed combination) and the co-administration of reference drugs that impact the bioavailability of the drugs when administered under fasting conditions. This is based on the approach established by the WHO for new fixed-dose combinations, in compliance with scenario 2 (World Health Organization. WHO Technical Report Series, No. 929, 2005). According to this scenario, it is necessary to demonstrate that the individual drugs have been administered together in the same doses and regimen in which the fixed-dose combination is intended to be administered, in addition to documenting that the safety and efficacy profile for this combination has been well characterized.

Thus, a single-center, open-label, two-period, two-treatment, two-sequence (AB and BA), crossover, randomized, single-dose comparative bioavailability study of an oral tablet preparation with the fixed combination of 4 mg glimepiride, 50 mg vildagliptin, and 1000 mg metformin hydrochloride (treatment B, test drug, test product of Laboratorios Silanes S. A. de C.V.) against co-administration of the reference drugs (reference drug (A)): Glimetal® (treatment A1 reference drug containing 4 mg glimepiride/1000 mg metformin hydrochloride, lot 19C105V2, product of Laboratorios Silanes S.A. de C.V.) and the reference drug vildagliptin (treatment A2) indicated by the COFEPRIS, in fasting healthy volunteers to determine bioequivalence in terms of speed and magnitude of absorption.

A total of 44 healthy volunteers (27 men and 17 women) were randomized in the study. 42 concluded their participation in the study and 2 withdrew their informed consent. The duration of the sampling time will be 48 hours, which was chosen considering the elimination half-life reported for glimepiride being the longest (7.5±4 hours in Mexican population). In this sense, after 4 half-lives, more than 90% of the administered dose of each drug will have been eliminated. The minimum washout period of 4 days was established according to the half-life elimination of glimepiride. After a period of 7 half-lives, the pharmacokinetic effect of washout can be completely disregarded. Each volunteer received the treatments under study according to randomization. Blood samples were collected and processed to obtain plasma before each administration (pre-dose sample) and at 0.25, 0.50, 1.00, 1.25, 1.50, 1.75, 2.00, 2.50, 3.00, 3.50, 4.00, 4.50, 5.00, 6.00, 8.00, 10.00, 12.00, 18.00, 24.00, 36.00, and 48 hours after administration of each drug. The samples from the volunteers were analyzed to quantify the three drugs using a high-performance liquid chromatography method, with protein precipitation as the extraction method, following a separation process on a reverse phase chromatographic column with mass spectrometry detection (HPLC-MS/MS) and as internal standard metformin HCl-d6, vildagliptin-d3, and glibenclamide, in plasma. The analytical method was previously validated under the parameters established in the Mexican Official Standard NOM-177-SSA1-2013 and was applied in this study for the characterization of the pharmacokinetic profiles.

(The notation used "reference drug (A)", "treatment (A2) reference drug", "treatment (B) test drug", and "treatment (A1) reference drug" is different from that used in the Example 5 of test and dilution profile).

TABLE 16

[]Descriptive statistics for plasma concentrations of vildagliptin with respect to time for treatment B (test drug)

| Time (h) | N | Mean (ng/ml) | SD (ng/ml) | SE (ng/ml) | Min (ng/ml) | Median (ng/ml) | Max (ng/ml) | CV % |
|---|---|---|---|---|---|---|---|---|
| 0.00 | 42 | 0.000 | 0.000 | 0.000 | 0.00 | 0.00 | 0.00 | — |
| 0.25 | 42 | 10.044 | 8.973 | 1.384 | 0.00 | 8.19 | 39.52 | 89.3 |
| 0.50 | 42 | 42.955 | 25.538 | 3.941 | 8.92 | 36.53 | 111.06 | 59.5 |
| 1.00 | 42 | 77.464 | 29.964 | 4.624 | 14.17 | 83.64 | 169.53 | 38.7 |
| 1.25 | 42 | 81.921 | 30.813 | 4.755 | 13.99 | 77.41 | 171.80 | 37.6 |
| 1.50 | 42 | 88.105 | 38.446 | 5.932 | 17.65 | 82.51 | 235.89 | 43.6 |
| 1.75 | 42 | 98.006 | 44.339 | 6.842 | 19.38 | 88.18 | 240.24 | 45.2 |
| 2.00 | 42 | 104.238 | 46.793 | 7.220 | 25.28 | 98.15 | 218.38 | 44.9 |
| 2.50 | 42 | 124.320 | 52.205 | 8.055 | 40.47 | 108.63 | 247.27 | 42.0 |
| 3.00 | 42 | 139.930 | 45.299 | 6.990 | 42.83 | 134.95 | 254.70 | 32.4 |
| 3.50 | 42 | 135.471 | 45.695 | 7.051 | 27.95 | 133.64 | 258.96 | 33.7 |
| 4.00 | 42 | 120.051 | 47.874 | 7.387 | 31.47 | 108.54 | 263.43 | 39.9 |
| 4.50 | 42 | 95.227 | 39.721 | 6.129 | 43.95 | 87.18 | 264.86 | 41.7 |
| 5.00 | 42 | 78.568 | 28.136 | 4.342 | 34.73 | 67.83 | 174.04 | 35.8 |
| 6.00 | 42 | 57.597 | 23.886 | 3.686 | 24.91 | 50.48 | 131.90 | 41.5 |
| 8.00 | 42 | 33.184 | 11.123 | 1.716 | 15.76 | 30.79 | 65.76 | 33.5 |
| 10.00 | 42 | 17.750 | 6.446 | 0.995 | 7.00 | 17.61 | 33.13 | 36.3 |
| 12.00 | 42 | 9.162 | 4.091 | 0.631 | 0.00 | 9.03 | 18.75 | 44.7 |
| 18.00 | 42 | 0.406 | 1.494 | 0.231 | 0.00 | 0.00 | 6.62 | 367.7 |
| 24.00 | 42 | 0.000 | 0.000 | 0.000 | 0.00 | 0.00 | 0.00 | |
| 36.00 | 41 | 0.000 | 0.000 | 0.000 | 0.00 | 0.00 | 0.00 | — |
| 48.00 | 42 | 0.000 | 0.000 | 0.000 | 0.00 | 0.00 | 0.00 | — |

TABLE 17

[]Descriptive statistics for plasma concentrations of glimepiride with respect to time for treatment B (test drug)

| Time (h) | N | Mean (ng/ml) | SD (ng/ml) | SE (ng/ml) | Min (ng/ml) | Median (ng/ml) | Max (ng/ml) | CV % |
|---|---|---|---|---|---|---|---|---|
| 0.00 | 42 | 0.000 | 0.000 | 0.000 | 0.00 | 0.00 | 0.00 | — |
| 0.25 | 42 | 6.763 | 13.420 | 2.071 | 0.00 | 0.00 | 61.20 | 198.4 |
| 0.50 | 42 | 41.037 | 51.737 | 7.983 | 0.00 | 22.19 | 202.10 | 126.1 |
| 1.00 | 42 | 88.913 | 74.516 | 11.498 | 5.92 | 69.84 | 319.80 | 83.8 |
| 1.25 | 42 | 97.221 | 74.375 | 11.476 | 6.60 | 79.31 | 310.71 | 76.5 |
| 1.50 | 42 | 99.154 | 71.758 | 11.073 | 8.68 | 82.98 | 322.70 | 72.4 |
| 1.75 | 42 | 105.110 | 76.704 | 11.830 | 10.17 | 82.00 | 370.40 | 73.0 |
| 2.00 | 42 | 106.944 | 73.223 | 11.299 | 16.24 | 86.27 | 344.80 | 68.5 |
| 2.50 | 42 | 115.604 | 67.249 | 10.377 | 33.70 | 98.60 | 331.77 | 58.2 |
| 3.00 | 42 | 124.261 | 66.828 | 10.312 | 37.09 | 117.06 | 317.55 | 53.8 |
| 3.50 | 42 | 127.945 | 61.896 | 9.551 | 40.06 | 130.70 | 285.60 | 48.4 |
| 4.00 | 42 | 132.327 | 61.718 | 9.523 | 45.51 | 132.30 | 282.10 | 46.6 |
| 4.50 | 42 | 137.172 | 50.283 | 7.759 | 50.55 | 130.26 | 244.12 | 36.7 |
| 5.00 | 42 | 104.295 | 36.731 | 5.668 | 36.83 | 103.27 | 194.00 | 35.2 |
| 6.00 | 42 | 71.554 | 24.766 | 3.821 | 29.35 | 70.40 | 122.12 | 34.6 |
| 8.00 | 42 | 57.017 | 22.170 | 3.421 | 19.76 | 57.80 | 117.77 | 38.9 |
| 10.00 | 42 | 43.984 | 15.458 | 2.385 | 16.19 | 41.95 | 84.32 | 35.1 |
| 12.00 | 42 | 33.495 | 11.240 | 1.734 | 14.99 | 32.87 | 65.30 | 33.6 |
| 18.00 | 42 | 13.263 | 4.496 | 0.694 | 7.47 | 12.25 | 24.90 | 33.9 |
| 24.00 | 42 | 12.265 | 6.663 | 1.028 | 0.00 | 11.35 | 27.39 | 54.3 |
| 36.00 | 41 | 4.680 | 6.081 | 0.950 | 0.00 | 0.00 | 19.24 | 129.9 |
| 48.00 | 42 | 1.601 | 3.761 | 0.580 | 0.00 | 0.00 | 17.55 | 234.9 |

TABLE 18

[]Descriptive statistics for plasma concentrations of metformin with respect to time for treatment B (test drug)

| Time (h) | N | Mean (ng/ml) | SD (ng/ml) | SE (ng/ml) | Min (ng/ml) | Median (ng/ml) | Max (ng/ml) | CV % |
|---|---|---|---|---|---|---|---|---|
| 0.00 | 42 | 0.000 | 0.000 | 0.00 | 0.00 | 0.00 | 0.00 | — |
| 0.25 | 42 | 427.205 | 215.518 | 33.255 | 36.77 | 390.66 | 953.56 | 50.4 |
| 0.50 | 42 | 1051.936 | 434.373 | 67.025 | 431.93 | 1031.46 | 2007.10 | 41.3 |
| 1.00 | 42 | 1588.913 | 563.927 | 87.016 | 586.59 | 1557.20 | 3071.61 | 35.5 |
| 1.25 | 42 | 1567.651 | 528.249 | 81.511 | 698.92 | 1538.51 | 2925.03 | 33.7 |
| 1.50 | 42 | 1558.951 | 465.147 | 71.774 | 724.78 | 1592.87 | 2812.11 | 29.8 |
| 1.75 | 42 | 1593.480 | 434.867 | 67.101 | 750.26 | 1579.39 | 2623.74 | 27.3 |
| 2.00 | 42 | 1600.398 | 417.239 | 64.381 | 810.47 | 1551.41 | 2537.79 | 26.1 |
| 2.50 | 42 | 1625.901 | 364.246 | 56.204 | 841.81 | 1555.14 | 2251.74 | 22.4 |
| 3.00 | 42 | 1663.037 | 402.349 | 62.084 | 816.56 | 1577.14 | 2566.13 | 24.2 |
| 3.50 | 42 | 1599.506 | 415.446 | 64.105 | 629.19 | 1561.56 | 2656.73 | 26.0 |
| 4.00 | 42 | 1551.503 | 424.092 | 65.439 | 682.09 | 1474.78 | 2599.53 | 27.3 |
| 4.50 | 42 | 1417.422 | 418.178 | 64.526 | 775.57 | 1328.03 | 2625.00 | 29.5 |
| 5.00 | 42 | 1263.759 | 360.643 | 55.648 | 736.06 | 1180.62 | 2239.04 | 28.5 |
| 6.00 | 42 | 956.532 | 266.147 | 41.067 | 563.13 | 909.30 | 1763.75 | 27.8 |
| 8.00 | 42 | 595.614 | 173.414 | 26.758 | 355.73 | 595.07 | 1202.16 | 29.1 |
| 10.00 | 42 | 334.341 | 102.274 | 15.781 | 175.05 | 336.70 | 656.09 | 30.6 |
| 12.00 | 42 | 209.386 | 60.269 | 9.300 | 123.13 | 201.43 | 354.41 | 28.8 |
| 18.00 | 42 | 75.118 | 18.193 | 2.807 | 43.16 | 71.22 | 127.38 | 24.2 |
| 24.00 | 42 | 36.933 | 9.062 | 1.398 | 20.01 | 36.27 | 58.78 | 24.5 |
| 36.00 | 41 | 11.254 | 13.120 | 2.049 | 0.00 | 0.00 | 34.70 | 116.6 |
| 48.00 | 42 | 1.162 | 5.331 | 0.823 | 0.00 | 0.00 | 28.34 | 458.8 |

To visualize possible differences between formulations and/or treatments, the plasma concentration profiles (±standard error) were plotted with respect to time, obtained in the participating volunteers (FIGS. 10-15) on an arithmetic and semi-logarithmic scale.

Descriptive Statistics of Pharmacokinetic Parameters

The pharmacokinetic parameters were determined through independent model methods. Descriptive statistics are presented below in Tables 19-21.

TABLE 19

[]Descriptive statistics of pharmacokinetic parameters of glimepiride by treatment (A: reference drug; B: test drug).

| Variable | Treatment | N | Geometric Mean | Mean | SD | SE | Min | Median | Max | C.V. % |
|---|---|---|---|---|---|---|---|---|---|---|
| $T_{max}$ (h) | A | 42 | 3.423 | 3.662 | 1.294 | 0.200 | 1.50 | 4.00 | 8.00 | 35.3 |
| | B | 42 | 3.239 | 3.548 | 1.241 | 0.192 | 1.00 | 4.00 | 5.00 | 35.0 |
| $C_{max}$ | A | 42 | 216.385 | 230.193 | 80.520 | 12.424 | 82.96 | 225.81 | 441.78 | 35.0 |
| (ng/mL) | B | 42 | 164.222 | 174.353 | 64.297 | 9.921 | 93.06 | 158.36 | 370.49 | 36.9 |
| $ABC_{0-t}$ | A | 42 | 1232.834 | 1273.681 | 333.485 | 51.458 | 574.33 | 1201.44 | 2222.49 | 26.2 |
| (h*ng/mL) | B | 42 | 1155.852 | 1207.939 | 358.671 | 55.344 | 685.95 | 1216.01 | 1867.16 | 29.7 |
| $ABC_{0-t}$ | A | 42 | 1323.282 | 1362.257 | 341.812 | 52.743 | 711.12 | 1295.90 | 2358.23 | 25.1 |
| (h*ng/mL) | B | 42 | 1273.565 | 1330.705 | 394.351 | 60.850 | 776.42 | 1337.79 | 2157.02 | 29.6 |
| $ABC_{\%EXTRAP}$ | A | 42 | 5.750 | 6.732 | 4.301 | 0.664 | 1.52 | 5.55 | 21.91 | 63.9 |
| (%) | B | 42 | 7.807 | 9.103 | 5.019 | 0.775 | 2.07 | 7.48 | 21.55 | 55.1 |
| $K_e$ (1/h) | A | 42 | 0.103 | 0.115 | 0.053 | 0.008 | 0.03 | 0.11 | 0.25 | 45.6 |
| | B | 42 | 0.089 | 0.101 | 0.046 | 0.007 | 0.02 | 0.10 | 0.23 | 46.0 |
| $T_{1/2}$ (h) | A | 42 | 6.704 | 7.654 | 4.638 | 0.716 | 2.78 | 6.33 | 26.38 | 60.6 |
| | B | 42 | 7.787 | 9.129 | 6.097 | 0.941 | 3.07 | 7.09 | 32.44 | 66.8 |

TABLE 20

[]Descriptive statistics of pharmacokinetic parameters of metformin by treatment (A: reference drug; B: test drug).

| Variable | Treat-ment | N | Geometric Mean | Mean | SD | SE | Min | Median | Max | C.V. % |
|---|---|---|---|---|---|---|---|---|---|---|
| $T_{max}$ (h) | A | 42 | 2.293 | 2.513 | 1.023 | 0.158 | 1.00 | 2.50 | 4.00 | 40.7 |
| | B | 42 | 2.208 | 2.476 | 1.149 | 0.177 | 1.00 | 2.50 | 6.00 | 46.4 |
| $C_{max}$ | A | 42 | 1955.279 | 2034.569 | 590.612 | 91.133 | 1184.30 | 1933.55 | 3529.75 | 29.0 |
| (ng/mL) | B | 42 | 1893.058 | 1958.858 | 502.007 | 77.461 | 848.66 | 1905.01 | 3071.61 | 25.6 |
| $ABC_{0-t}$ | A | 42 | 12602.401 | 12962.823 | 3144.641 | 485.229 | 6966.76 | 12111.49 | 20295.08 | 24.3 |

TABLE 20-continued

[]Descriptive statistics of pharmacokinetic parameters of metformin by treatment (A: reference drug; B: test drug).

| Variable | Treatment | N | Geometric Mean | Mean | SD | SE | Min | Median | Max | C.V. % |
|---|---|---|---|---|---|---|---|---|---|---|
| (h*ng/mL) | B | 42 | 12321.994 | 12607.936 | 2719.863 | 419.684 | 7638.77 | 12271.24 | 18508.01 | 21.6 |
| $ABC_{0-t}$ | A | 42 | 12833.583 | 13185.175 | 3133.841 | 483.562 | 7345.32 | 12402.47 | 20540.69 | 23.8 |
| (h*ng/mL) | B | 42 | 12587.307 | 12873.205 | 2764.212 | 426.527 | 7857.69 | 12454.55 | 18792.97 | 21.5 |
| $ABC_{\%EXTRAP}$ | A | 42 | 1.627 | 1.797 | 0.897 | 0.138 | 0.66 | 1.67 | 5.15 | 49.9 |
| (%) | B | 42 | 1.748 | 2.090 | 1.841 | 0.284 | 0.90 | 1.54 | 10.74 | 88.1 |
| $K_e$ (1/h) | A | 42 | 0.140 | 0.146 | 0.037 | 0.006 | 0.07 | 0.15 | 0.23 | 25.4 |
| | B | 42 | 0.132 | 0.146 | 0.048 | 0.007 | 0.02 | 0.16 | 0.22 | 33.0 |
| $T_{1/2}$ (h) | A | 42 | 4.936 | 5.153 | 1.682 | 0.260 | 3.06 | 4.58 | 10.35 | 32.6 |
| | B | 42 | 5.245 | 6.570 | 7.249 | 1.119 | 3.19 | 4.43 | 38.44 | 110.3 |

TABLE 21

[] Descriptive statistics of pharmacokinetic parameters of vildagliptin by treatment (A: reference drug; B: test drug).

| Variable | Treatment | N | Geometric Mean | Mean | SD | SE | Min | Median | Max | C.V. % |
|---|---|---|---|---|---|---|---|---|---|---|
| $T_{max}$ (h) | A | 42 | 2.630 | 2.929 | 1.213 | 0.187 | 0.50 | 3.00 | 6.00 | 41.4 |
| | B | 42 | 3.010 | 3.185 | 1.014 | 0.156 | 1.00 | 3.00 | 6.00 | 31.8 |
| $C_{max}$ | A | 42 | 168.931 | 180.158 | 67.513 | 10.417 | 85.18 | 154.35 | 326.53 | 37.5 |
| (ng/mL) | B | 42 | 160.107 | 167.616 | 50.399 | 7.777 | 78.24 | 166.87 | 264.86 | 30.1 |
| $ABC_{0-t}$ | A | 42 | 718.085 | 736.562 | 177.932 | 27.455 | 483.82 | 699.51 | 1331.00 | 24.2 |
| (h*ng/mL) | B | 42 | 703.987 | 722.076 | 167.251 | 25.807 | 454.71 | 704.19 | 1166.48 | 23.2 |
| $ABC_{0-t}$ | A | 42 | 753.116 | 771.915 | 182.266 | 28.124 | 498.85 | 734.76 | 1386.84 | 23.6 |
| (h*ng/mL) | B | 42 | 735.860 | 752.532 | 164.280 | 25.349 | 486.47 | 735.99 | 1197.32 | 21.8 |
| $ABC_{\%EXTRAP}$ | A | 42 | 4.143 | 4.623 | 2.343 | 0.362 | 1.30 | 4.14 | 12.80 | 50.7 |
| (%) | B | 42 | 3.843 | 4.308 | 2.113 | 0.326 | 1.19 | 3.62 | 8.99 | 49.0 |
| $K_e$ (1/h) | A | 42 | 0.298 | 0.305 | 0.062 | 0.010 | 0.17 | 0.31 | 0.42 | 20.4 |
| | B | 42 | 0.303 | 0.310 | 0.067 | 0.010 | 0.21 | 0.30 | 0.50 | 21.5 |
| $T_{1/2}$ (h) | A | 42 | 2.323 | 2.379 | 0.552 | 0.085 | 1.64 | 2.22 | 4.14 | 23.2 |
| | B | 42 | 2.285 | 2.336 | 0.500 | 0.077 | 1.38 | 2.27 | 3.23 | 21.4 |

Confidence Intervals and Borderline Tests for Pharmacokinetic Parameters

TABLE 22

[]Confidence intervals and borderline tests for log-transformed pharmacokinetic parameters of glimepiride (Treatment A vs. Treatment B)

| Pharmacokinetic | Reference (A)* | Test (B)* | Ratio of Averages [B/A] | Classical Confidence Interval | | Schuirmann's one-sided double t-test | | Anderson | |
|---|---|---|---|---|---|---|---|---|---|
| Parameter | Average | Average | (%) | Lower | Upper | P < 80 | P > 125 | Hauck test | Power |
| Ln ($C_{max}$) | 216.707 | 164.067 | 75.71 | 68.38 | 83.82 | 0.8163 | 0.0000 | 0.8163 | 0.9742 |
| Ln ($ABC_{0-t}$) | 1230.492 | 1156.671 | 94.00 | 88.80 | 99.51 | 0.0000 | 0.0000 | 0.0000 | 1.0000 |
| | Criteria | | | >80 | <125 | <0.05 | <0.05 | <0.05 | >0.8 |

*Geometric average

TABLE 23

Intrasubject variability and coefficients of variability for pharmacokinetic parameters of glimepiride

| Pharmacokinetic Parameter | Intrasubject Variability Coefficient (%) |
|---|---|
| Ln ($C_{max}$) | 28.21 |
| Ln ($ABC_{0-t}$) | 15.58 |

TABLE 24

[]Confidence intervals and borderline tests for log-transformed pharmacokinetic parameters of metformin (Treatment A vs. Treatment B)

| Pharmacokinetic Parameter | Reference (A)* Average | Test (B)* Average | Ratio of Averages [B/A] (%) | Classical Confidence Interval Lower | Upper | Schuirmann's one-sided double t-test P < 80 | P > 125 | Anderson Hauck test | Power |
|---|---|---|---|---|---|---|---|---|---|
| Ln ($C_{max}$) | 1959.488 | 1897.582 | 96.84 | 90.56 | 103.55 | 0.0000 | 0.0000 | 0.0000 | 0.9998 |
| Ln ($ABC_{0-t}$) | 12622.141 | 12368.848 | 97.99 | 93.08 | 103.16 | 0.0000 | 0.0000 | 0.0000 | 1.0000 |
| Criteria | | | | >80 | <125 | <0.05 | <0.05 | <0.05 | >0.8 |

*Geometric average

TABLE 25

Intrasubject variability and coefficients of variability for pharmacokinetic parameters of metformin

| Pharmacokinetic Parameter | Intrasubject Variability Coefficient (%) |
|---|---|
| Ln ($C_{max}$) | 18.37 |
| Ln ($ABC_{0-t}$) | 14.05 |

TABLE 26

[]Confidence intervals and borderline tests for log-transformed pharmacokinetic parameters of vildagliptin (Treatment A vs. Treatment B)

| Pharmacokinetic Parameter | Reference (A)* Average | Test (B)* Average | Ratio of Averages [B/A] (%) | Classical Confidence Interval Lower | Upper | Schuirmann's one-sided double t-test P < 80 | P > 125 | Anderson Hauck test | Power |
|---|---|---|---|---|---|---|---|---|---|
| Ln ($C_{max}$) | 169.256 | 160.703 | 94.95 | 88.55 | 101.80 | 0.0001 | 0.0000 | 0.0001 | 0.9997 |
| Ln ($ABC_{0-t}$) | 718.554 | 705.309 | 98.16 | 94.92 | 101.51 | 0.0000 | 0.0000 | 0.0000 | 1.0000 |
| Criteria | | | | >80 | <125 | <0.05 | <0.05 | <0.05 | >0.8 |

*Geometric average

TABLE 27

Intrasubject variability and coefficients of variability for pharmacokinetic parameters of vildagliptin

| Pharmacokinetic Parameter | Intrasubject Variability Coefficient (%) |
|---|---|
| Ln ($C_{max}$) | 19.12 |
| Ln ($ABC_{0-t}$) | 9.14 |

ADVANTAGES AND APPLICATIONS OF THE INVENTION

The invention relates to an innovative fixed combination drug of increased efficacy comprising a sulfonylurea, a dipeptidyl peptidase-4 (DPP4) inhibitor, and a biguanidine for improved management of type 2 diabetes mellitus.

The sulfonylurea, dipeptidyl peptidyl peptidase-4 (DPP4) inhibitor, and biguanidine used for the manufacture of said drug product and adapted to be of immediate release are glimepiride, vildagliptin, and metformin in its hydrochloride form.

At the same time, this invention allows solving a set of important technological challenges in the manufacture of said drug product due to the physicochemical properties and the difference in dosage of the synergistic combination of the drugs sulfonylurea, dipeptidyl peptidase-4 (DPP4) inhibitor, and biguanidine comprising to ensure obtaining a stable product for such purposes. The drug product comprises: (a) a sulfonylurea, (b) a dipeptidyl peptidase-4 (DPP4) inhibitor, and (c) a biguanide, or a pharmaceutical salt of any of the same, in pharmaceutically acceptable amounts in the range between 1-4 mg, 50 mg, and 500-1000 mg respectively, in combination with pharmaceutically acceptable excipients and/or vehicles.

What is claimed is:

1. A combination drug in the form of a single solid immediate-release dosage unit, comprising:

(a) glimepiride, (b) vildagliptin, and (c) metformin hydrochloride, or a pharmaceutical salt of any of the same, in pharmaceutically acceptable amounts in the range between 1-4 mg, 50 mg, and 500-1000 mg respectively, wherein the components (a), (b) and (c) are co-formulated within a single homogeneous solid matrix;

and further comprising an excipient system comprising:

microcrystalline cellulose PH 101 as a diluent, crospovidone as a disintegrant, magnesium aluminum metasilicate as an adsorbent, and poloxamer 188 as a solubilizer, optionally in combination with one or more pharmaceutically acceptable excipients and/or vehicles selected from the group of binders, lubricants, solvents and/or coatings;

wherein the excipient system is configured to provide immediate release of each of the components (a), (b) and (c) from said dosage unit; and wherein said drug product is further in solid form selected from tablet, caplet, granules, lozenges and pills.

2. The combination drug, according to claim 1, wherein the (a) glimepiride, the (b) vildagliptin, and the (c) metformin hydrochloride, or a pharmaceutical salt of any of the same, are in the pharmaceutically acceptable amounts of 1/50/500 mg respectively.

3. The combination drug, according to claim 1, wherein the (a) glimepiride, the (b) vildagliptin, and the (c) metformin hydrochloride, or a pharmaceutical salt of any of the same, are in the pharmaceutically acceptable amounts of 2/50/1000 mg respectively.

4. The combination drug, according to claim 1, wherein the (a) glimepiride, the (b) vildagliptin, and the (c) metformin hydrochloride, or a pharmaceutical salt of any of the same, are in the pharmaceutically acceptable amounts of 4/50/1000 mg respectively.

5. The combination drug, according to claim 1, wherein the microcrystalline cellulose PH 101 is present in a pharmaceutically acceptable amount in the range of 5 to 90% by weight of the combination drug.

6. The combination drug, according to claim 1, wherein the crospovidone is present in a pharmaceutically acceptable amount in the range of 0.5-15% by weight of the combination drug.

7. The combination drug, according to claim 1, wherein the magnesium aluminum metasilicate is present in a pharmaceutically acceptable amount in the range of 0.5-90% by weight of the combination drug.

8. The combination drug, according to claim 1, wherein the binder is present and is polyvidone K90 in a pharmaceutically acceptable amount in the range of 0.5 to 5% by weight of the combination drug.

9. The combination drug, according to claim 1, wherein the poloxamer 188 is present in a pharmaceutically acceptable amount in the range of 0.01 to 5% by weight of the combination drug.

10. The combination drug, according to claim 1, wherein the lubricant is present and is magnesium stearate in a pharmaceutically acceptable amount in the range of 0.25 to 10% by weight of the combination drug.

11. The combination drug, according to claim 1, wherein the coating is present and is a moisture and light barrier coating.

12. The combination drug, according to claim 11, wherein the moisture and light barrier coating is Opadry AMB II in a pharmaceutically acceptable amount in the range of 0.5 to 6% by weight of the combination drug.

13. The combination drug, according to claim 1, wherein the solvent is present and is water in a pharmaceutically acceptable quantity.

14. A method of manufacturing the combination drug according to claim 1, comprising the steps of: combining (a) glimepiride, (b) vildagliptin, and (c) metformin hydrochloride, or a pharmaceutical salt of any of the same, in pharmaceutically acceptable amounts in the range between 1-4 mg, 50 mg, and 500-1000 mg respectively, with the excipient system comprising:

the microcrystalline cellulose PH 101 as a diluent, the crospovidone as a disintegrant, the magnesium aluminum metasilicate as an adsorbent, and the poloxamer 188 as a solubilizer, optionally in combination with the one or more pharmaceutically acceptable excipients and/or vehicles selected from the group of the binders, the lubricants, the solvents and/or the coatings.

15. A method for the control and management of type 2 diabetes mellitus in individuals, the method comprising:

administering the combination drug according to claim 1 to individuals requiring triple oral therapy for treatment of type 2 diabetes mellitus.

* * * * *